US008929978B2

(12) United States Patent
Khan et al.

(10) Patent No.: US 8,929,978 B2
(45) Date of Patent: *Jan. 6, 2015

(54) PHOTOTHERAPY DEVICES AND METHODS COMPRISING OPTIONALLY SUBSTITUTED TERPHENYL AND QUATERPHENYL COMPOUNDS

(75) Inventors: Sazzadur Rahman Khan, San Diego, CA (US); Shijun Zheng, San Diego, CA (US); Amane Mochizuki, Carlsbad, CA (US); Liping Ma, San Diego, CA (US)

(73) Assignee: Nitto Denko Corporation, Osaka (JP)

( * ) Notice: Subject to any disclaimer, the term of this patent is extended or adjusted under 35 U.S.C. 154(b) by 510 days.

This patent is subject to a terminal disclaimer.

(21) Appl. No.: 13/359,323

(22) Filed: Jan. 26, 2012

(65) Prior Publication Data

US 2012/0197179 A1 Aug. 2, 2012

Related U.S. Application Data

(60) Provisional application No. 61/496,385, filed on Jun. 13, 2011, provisional application No. 61/436,821, filed on Jan. 27, 2011.

(51) Int. Cl.
*A61N 5/06* (2006.01)
*C07D 235/18* (2006.01)
*C09K 11/06* (2006.01)
*C07D 403/10* (2006.01)

(52) U.S. Cl.
CPC ........ *A61N 5/062* (2013.01); *C09K 2211/1014* (2013.01); *C09K 2211/1011* (2013.01); *C09K 2211/1044* (2013.01); *A61N 2005/0645* (2013.01); *C09K 2211/1007* (2013.01); *C07D 235/18* (2013.01); *A61N 2005/0653* (2013.01); *C09K 11/06* (2013.01); *C07D 403/10* (2013.01); *Y10S 428/917* (2013.01)
USPC .......... 604/20; 607/88; 607/90; 607/91; 607/92; 428/690; 428/917; 313/504; 313/505; 313/506; 257/40; 257/E51.05; 257/E51.026; 257/E51.032

(58) Field of Classification Search
None
See application file for complete search history.

(56) References Cited

U.S. PATENT DOCUMENTS

| 6,620,529 B1 | 9/2003 | Ise et al. |
| 6,835,469 B2 | 12/2004 | Kwong et al. |

(Continued)

FOREIGN PATENT DOCUMENTS

| CN | 101 400 658 | 4/2009 |
| GB | 2 408 209 | 5/2005 |

(Continued)

OTHER PUBLICATIONS

Peng et al., "5-Aminolevulinic Acid-Based Photodynamic Therapy. Clinical Research and Future Challenges", *Cancer*, Jun. 15, 1997, vol. 79, No. 12, pp. 2282-2308.

(Continued)

*Primary Examiner* — Gregory Clark
(74) *Attorney, Agent, or Firm* — Knobbe, Martens, Olson & Bear, LLP

(57) ABSTRACT

Methods and devices related to the treatment of diseases using phototherapy are described. Some embodiments provide an organic light-emitting diode device, such as a light-emitting device for phototherapy, comprising Ring system 1, Ring system 2, Ring system 3, or Ring system 4. Methods of treating disease with phototherapy are also described.

21 Claims, 11 Drawing Sheets

(56) References Cited

U.S. PATENT DOCUMENTS

| | | |
|---|---|---|
| 7,678,959 B2 | 3/2010 | Okada et al. |
| 8,426,040 B2 | 4/2013 | Zheng et al. |
| 2005/0106710 A1* | 5/2005 | Friedman et al. .......... 435/287.1 |
| 2008/0014464 A1 | 1/2008 | Kawamura et al. |
| 2008/0311178 A1 | 12/2008 | Ishikura et al. |
| 2009/0134783 A1 | 5/2009 | Lin et al. |
| 2010/0060154 A1 | 3/2010 | Nomura et al. |
| 2010/0326526 A1 | 12/2010 | Zheng |
| 2011/0251401 A1 | 10/2011 | Zheng et al. |
| 2012/0104277 A1* | 5/2012 | Morren .................... 250/455.11 |
| 2012/0197179 A1 | 8/2012 | Khan et al. |

FOREIGN PATENT DOCUMENTS

| | | |
|---|---|---|
| WO | WO 2004/020388 | 3/2004 |
| WO | WO 2006/101735 | 9/2006 |
| WO | WO 2006/130302 | 12/2006 |
| WO | WO 2008/052350 | 5/2008 |
| WO | WO 2009/103165 | 8/2009 |
| WO | WO 2010/044607 | 4/2010 |
| WO | WO 2011/008560 | 1/2011 |
| WO | WO 2011/109671 | 9/2011 |
| WO | WO 2012/009283 | 1/2012 |
| WO | WO 2012/103380 | 8/2012 |

OTHER PUBLICATIONS

Chen et al., "Versatile, Benzimidazole/Amine-Based Ambipolar Compounds for Electroluminescent Applications: Single-Layer, Blue, Fluorescent OLEDs, Hosts for Single-Layer, Phosphorescent OLEDs", Advanced Functional Materials, 2009, vol. 19, pp. 2661-2670.

Gustafsson et al. "Flexible Light-Emitting Diodes Made from Soluble Conducting Polymer," Nature, Jun. 11, 1992, vol. 357, pp. 477-479.

Kreimer-Birnbaum et al., "Modified Porphyrins, Chlorins, Phthalocyanines and Purpurins: Second-Generation Photosensitizers for Photodynamic Therapy", Semin Hematol, 1989, vol. 26, pp. 157-173.

Li et al., "Synthesis and Functional Properties of Strongly Luminescent Diphenylamino End-Capped Oligophenylenes", American Chemical Society, 2004, vol. 69, pp. 921-927.

International Search Report and Written Opinion in PCT Application No. PCT/US2012/022792, dated May 7, 2012.

* cited by examiner

No ALA + 30J/cm$^2$

1mM ALA + 30J/cm$^2$

PHOTOTHERAPY DEVICES AND METHODS COMPRISING OPTIONALLY SUBSTITUTED TERPHENYL AND QUATERPHENYL COMPOUNDS

CROSS-REFERENCE TO RELATED APPLICATIONS

This application claims priority to U.S. Provisional Patent Application No. 61/496,385, filed Jun. 13, 2011 and U.S. Provisional Patent Application No. 61/436,821, filed Jan. 27, 2011. Both of which are incorporated by reference herein in their entireties.

BACKGROUND

1. Field

The embodiments relate to light-emitting devices, such as those containing organic light-emitting diodes, for uses such as phototherapy.

2. Description of the Related Art

Phototherapy may be useful in treating a number of medical conditions. However, light sources such as lasers, which may be used for phototherapy, may be expensive, difficult to transport, and not suitable for home or outpatient treatment. Therefore, there may be a need for alternative sources of light for phototherapy which may be less expensive and more portable.

SUMMARY

Some embodiments relate to organic light-emitting devices which may be used for phototherapy. These devices typically comprise an organic light-emitting diode, such as an organic light-emitting diode comprising an anode, a cathode, and an organic light-emitting layer disposed between the anode and the cathode. In some embodiments, the organic light-emitting layer may comprise a light-emitting component, such as a fluorescent or a phosphorescent compound, which may include an optionally substituted terphenyl or quaterphenyl compound, such as a compound described herein. In some embodiments, the light-emitting layer may comprise a host compound, such as a substituted interphenylene compound, including a compound described herein. Some devices may also comprise wavelength convertor.

Some embodiments relate to a device for use in phototherapy comprising: an organic light-emitting diode comprising a compound comprising an optionally substituted ring system selected from the group consisting of:

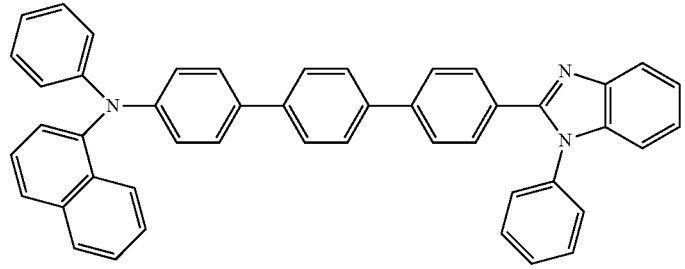

(Ring system 1)

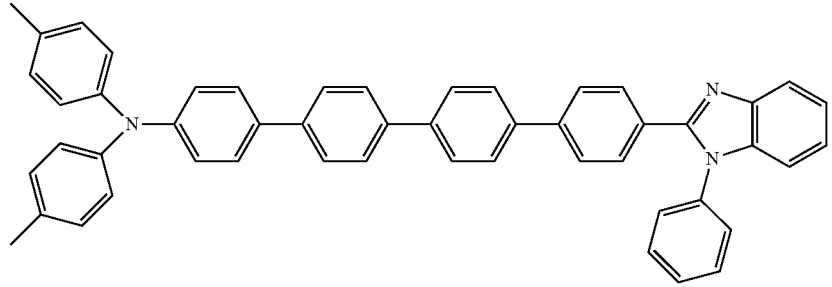

(Ring system 2)

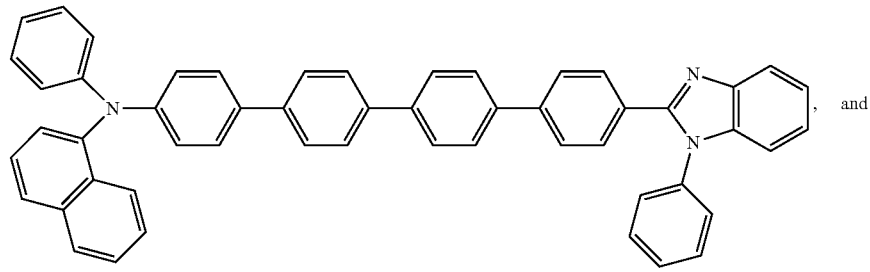

(Ring system 3)

, and

-continued

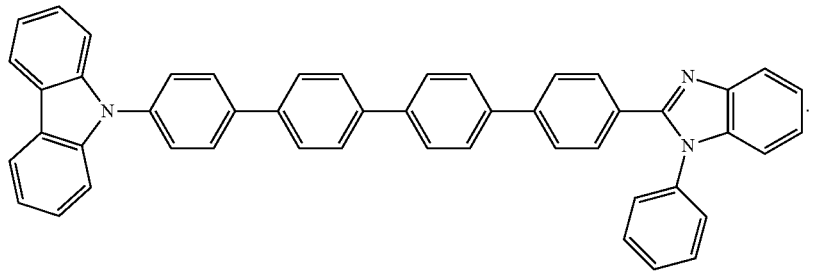

(Ring system 4)

The device may be configured to emit a therapeutically effective amount of light to a mammal. The device may further be part of a phototherapy system that includes the device and a wound dressing.

In some embodiments, these devices may be used in a method of carrying out phototherapy comprising: exposing at least a portion of a tissue of a mammal to light from a device described herein. In some embodiments, the tissue comprises a photosensitive compound which may not be naturally in the tissue, and at least a portion of the photosensitive compound may be activated by exposing the portion of the tissue to light from the device.

Some embodiments provide a method of treating a disease, comprising: exposing at least a portion of a tissue of a mammal in need thereof to light from a device described herein. In some embodiments, the tissue comprises a photosensitive compound which may not naturally be in the tissue, and at least a portion of the photosensitive compound may be activated by exposing the portion of the tissue to light from the device to thereby treat the disease.

In some embodiments, a method of treating a disease may comprise administering a photosensitive compound to a tissue of a mammal in need thereof; and exposing at least a portion of the tissue to light from a device described herein; wherein at least a portion of the photosensitive compound is activated by at least a portion of the light from the device to which the tissue is exposed, to thereby treat the disease.

Some embodiments provide a phototherapy system comprising: a device described herein; and a photosensitive compound; wherein the photosensitive compound is suitable for administration to a tissue of a mammal in need of phototherapy; and wherein the device is configured to emit light of a wavelength which can activate at least a portion of the photosensitive compound when it is in the tissue.

These and other embodiments are described in greater detail below.

DETAILED DESCRIPTION OF THE PREFERRED EMBODIMENTS

Figure 1:
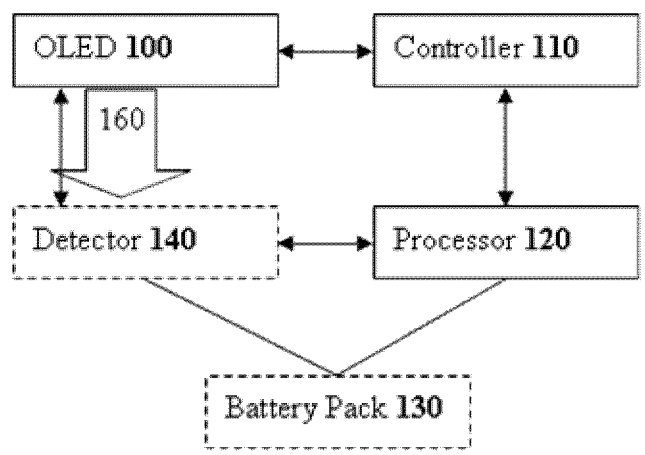
FIG. 1 is a schematic diagram of an embodiment of a device described herein.

Unless otherwise indicated, when a chemical structural feature such as aryl is referred to as being "optionally substituted," it is meant that the feature may have no substituents (i.e. be unsubstituted) or may have one or more substituents. A feature that is "substituted" has one or more substituents. The term "substituent" has the ordinary meaning known to one of ordinary skill in the art. In some embodiments, the substituent is a halogen, or has from 1-20 carbon atoms, from 1-10 carbon atoms, or has a molecular weight of less than about 500, about 300, or about 200. In some embodiments, the substituent has at least 1 carbon atom or at least 1 heteroatom, and has about 0-10 carbon atoms and about 0-5 heteroatoms independently selected from: N, O, S, F, Cl, Br, I, and combinations thereof. In some embodiments, each substituent consists of about 0-20 carbon atoms, about 0-47 hydrogen atoms, about 0-5 oxygen atoms, about 0-2 sulfur atoms, about 0-3 nitrogen atoms, about 0-1 silicon atoms, about 0-7 fluorine atoms, about 0-3 chlorine atoms, about 0-3 bromine atoms, and about 0-3 iodine atoms. Examples include, but are not limited to, alkyl, alkenyl, alkynyl, carbazolyl, cycloalkyl, cycloalkenyl, cycloalkynyl, aryl, diarylamino, heteroaryl, heteroalicyclyl, aralkyl, heteroaralkyl, (heteroalicyclyl)alkyl, hydroxy, protected hydroxy, alkoxy, aryloxy, acyl, ester, mercapto, alkylthio, arylthio, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxyl, trihalomethanesulfonyl, trihalomethanesulfonamido, and amino, including mono- and di-substituted amino groups, and the protected derivatives thereof.

In some embodiments, the substituents may include, but are not limited to, $C_{1-10}$ alkyl such as methyl, ethyl, propyl isomers (e.g. n-propyl and isopropyl), cyclopropyl, butyl isomers, cyclobutyl isomers (e.g. cyclobutyl, methylcyclopropyl, etc.), pentyl isomers, cyclopentyl isomers, hexyl isomers, cyclohexyl isomers, heptyl isomer, cycloheptyl isomers, etc; alkoxy such as —$OCH_3$, —$OC_2H_5$, —$OC_3H_7$, —$OC_4H_9$, —$OC_5H_{11}$, —$OC_6H_{13}$, —$OC_7H_{15}$, etc.; halo, such as F, Cl, Br, I, etc.; $C_{1-10}$ haloalkyl, including perfluoroalkyl such as —$CF_3$, —$C_2F_5$, —$C_3F_7$, —$C_4F_9$, etc.; $C_{1-10}$ acyl such as formyl, acetyl, benzoyl, etc.; $C_{1-10}$ amides attaching at the carbonyl or nitrogen atom such as —$NCOCH_3$, —$CONHCH_2$, etc.; $C_{1-10}$ esters attaching at the carbonyl or oxygen atom such as —$OCOCH_3$, —$CO_2CH_2$, etc.; $C_{1-10}$ carbamates attaching at the nitrogen atom or oxygen atom; cyano; cyanate; isocyanate; nitro; etc.

In some embodiments, the substituents may be selected from: F, Cl, $C_{1-6}$ alkyl, —O—$C_{1-6}$ alkyl, CN, $NO_2$, and $CF_3$.

In some embodiments, the compounds may consist essentially of: a Ring system 1, Ring system 2, Ring system 3, or Ring system 4, each without substituents, or Ring system 1, Ring system 2, Ring system 3, or Ring system 4, each with one or more substituents on the ring system. In some embodiments, Ring system 1, Ring system 2, Ring system 3, or Ring system 4 may each have 1, 2, 3, 4, 5, 6, 7, 8, 9, or 10 substituents.

The term "work function" has the ordinary meaning known to one of ordinary skill in the art. In some embodiments, the "work function" of a metal refers to a measure of the minimum energy required to extract an electron from the surface of the metal.

The term "high work function metal" has the ordinary meaning known to one of ordinary skill in the art. In some embodiments, a "high work function metal" includes a metal or alloy that easily injects holes and typically has a work function greater than or equal to 4.5.

The term "low work function metal" has the ordinary meaning known to one of ordinary skill in the art. In some embodiments, a "low work function metal" includes a metal or alloy that easily loses electrons and typically has a work function less than 4.3.

The compounds and compositions described herein can be incorporated into light-emitting devices in various ways. For example, an embodiment provides an organic component disposed between an anode and a cathode. In some embodiments, the device may be configured so that holes can be transferred from the anode to the organic component. In some embodiments, the device may be configured so that electrons can be transferred from the cathode to the organic component. The organic component may comprise the compounds and/or compositions described herein. For example, a compound described herein may be a host in an emissive layer, a host in a layer that is not an emissive layer, or may be a light-emitting component in an emissive layer.

An organic component may comprise one or more layers comprising organic materials such as an emissive layer, a hole-transport layer, an electron-transport layer, a hole-injection layer, an electron injection layer, etc. In some embodiments, the compounds described may be used as an emissive compound, as an ambipolar host in an organic light-emitting diode emissive layer, or both. In some embodiments, the compounds disclosed herein may provide well balanced hole-transport and electron-transport mobility, which may lead to a simpler device structure with high quantum efficiency and low turn-on voltage. For example in some embodiments, the organic light-emitting diode or device incorporating the presently described compounds may not have a hole transporting layer or an emissive layer. In some embodiments, these compounds may have high electrochemical stability, high thermal stability, a high glass transition temperature (Tg), and high photostability. Thus, these compounds may provide an OLED device with a longer lifetime than existing OLED devices.

Figure 2:
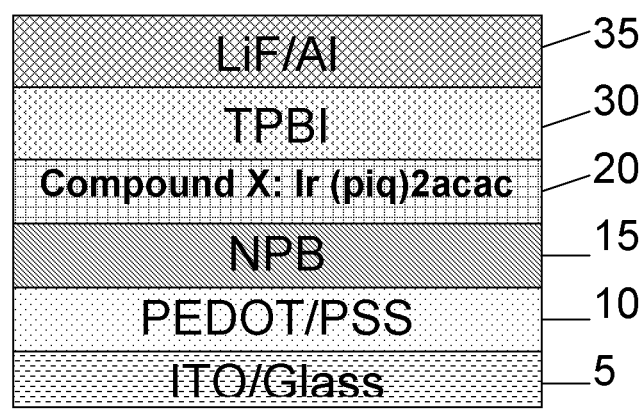
FIG. 2 is a schematic diagram of an embodiment of a device described herein.

An example of a configuration of an embodiment of a device comprising a compound described herein is shown in FIG. 2. The device comprises the following layers in the order given: an anode 5, a hole-injection layer 10, a hole-transport layer 15, a light-emitting layer 20, an electron-transport layer 30, and a cathode 35.

Figure 3:
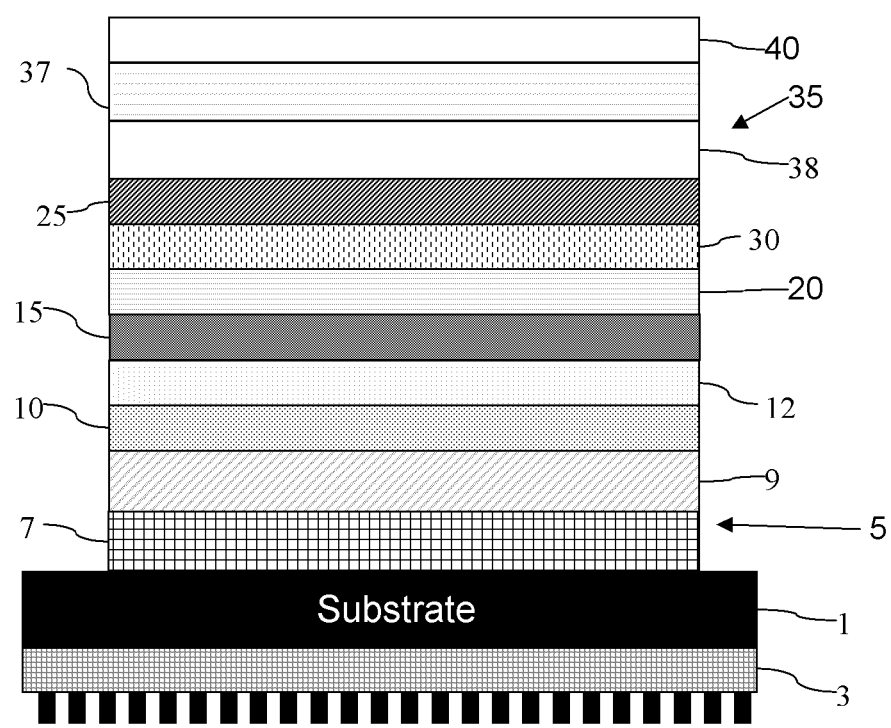
FIG. 3 is a schematic diagram of an embodiment of a device described herein.
Figure 4:
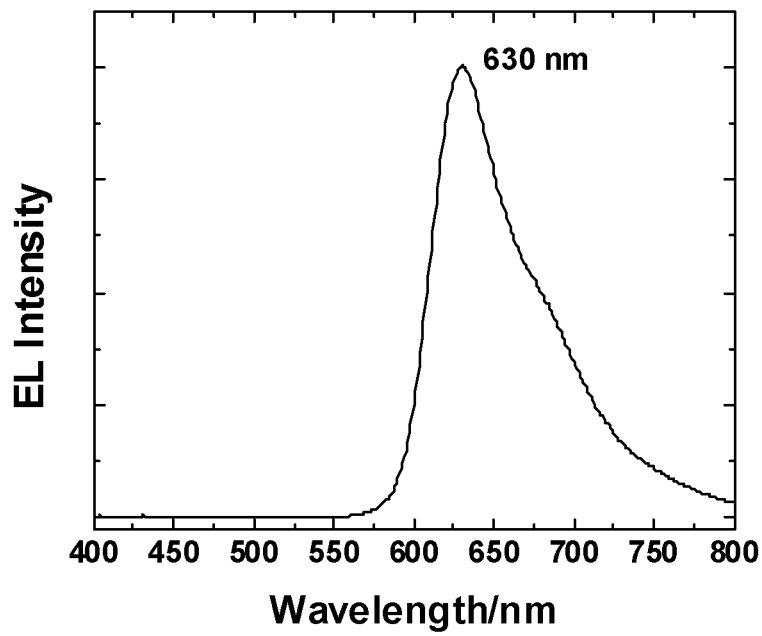
FIG. 4 is the electroluminescence spectrum of an embodiment of a light-emitting device.
Figure 5:
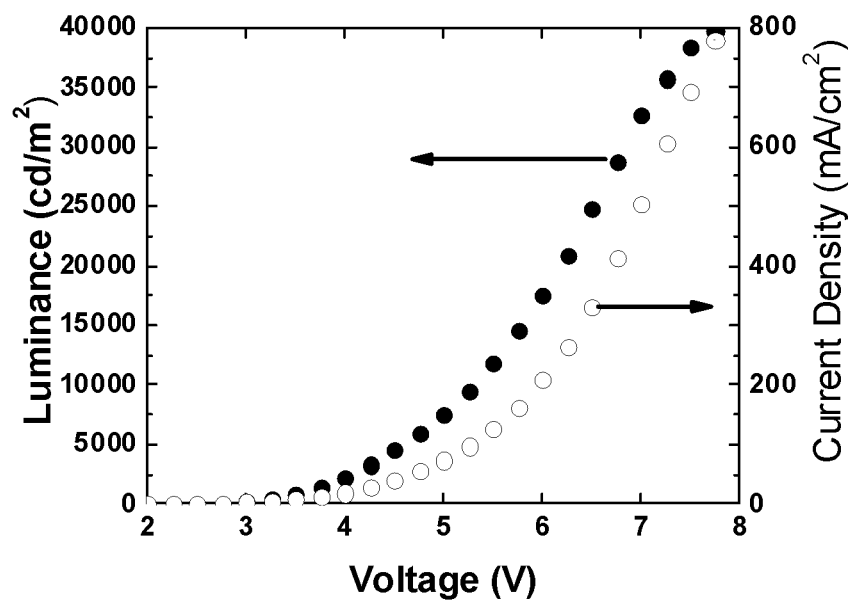
FIG. 5 is a plot of current density/brightness vs. voltage curve of an embodiment of a light-emitting device.
Figure 6:
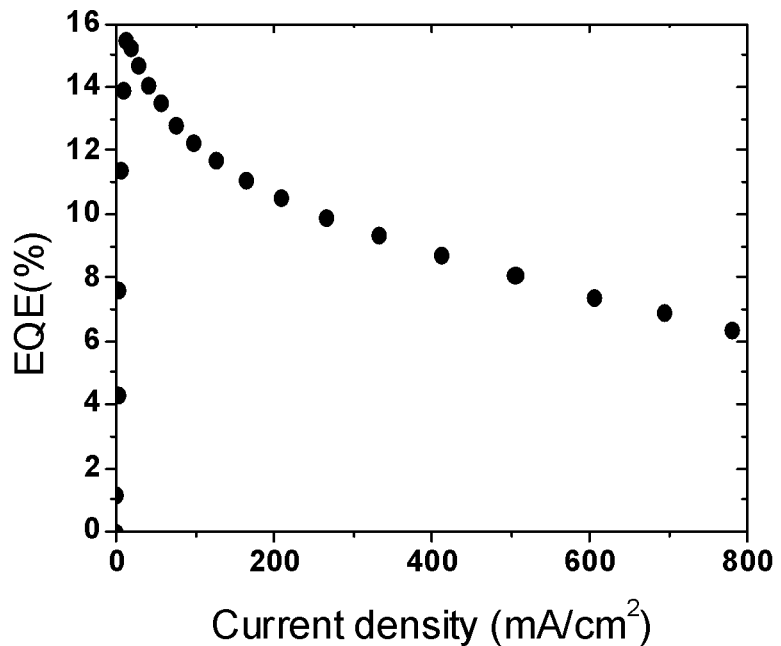
FIG. 6 is a plot of the EQE (external quantum efficiency) with respect to the current density of an embodiment of a light-emitting device.

Some embodiments may have a structure as represented schematically by FIG. 3. A light-emitting layer 20 is disposed between an anode 5 and cathode 35. The cathode 35 may comprise two cathode sublayers: a first cathode sublayer 37, and a second cathode sublayer 38 disposed between the first cathode sublayer 37 and the light-emitting layer 20. The anode 5 may comprise two anode sublayers: a first anode sublayer 7, and a second anode sublayer 9 disposed between the first anode sublayer 7 and the light-emitting layer 20. An optional electron-injecting layer 25 may be disposed between the cathode 35 or the second cathode sublayer 38 and the light-emitting layer 20. An optional electron-transport layer 30 may be disposed between the light-emitting layer 20 and the cathode 35, the second cathode sublayer 38, or the electron-injection layer 25. An optional hole-injecting layer 10 may be disposed between the light-emitting layer 20 and the anode 5 or the second anode sublayer 9. An optional p-doped hole-injecting layer 12 may be disposed between the hole-injecting layer 10 the emissive layer 20. An optional hole-transport layer 15 may be disposed between the hole-injecting layer 10 or the p-doped hole-injecting layer 12 and the light-emitting layer 20. The anode 5 may optionally be disposed on a substrate 1, and the substrate 1 may optionally be disposed on a heat dissipation layer 3. A capping layer 40 may optionally be disposed on the cathode 35.

An anode layer, e.g. anode 5, may comprise a conventional material such as a metal, mixed metal, alloy, metal oxide or mixed-metal oxide, or a conductive polymer. Examples of suitable metals include the metals in Groups 10, Group 11, and Group 12 transition metals. If the anode layer is to be light-transmitting, mixed-metal oxides of Groups 12, Group 13, and Group 14 metals or alloys thereof, such as zinc oxide, tin oxide, indium zinc oxide (IZO) or indium-tin-oxide (ITO) may be used. The anode layer may include an organic material such as polyaniline, e.g., as described in "Flexible light-emitting diodes made from soluble conducting polymer," Nature, vol. 357, pp. 477-479 (11 Jun. 1992). Examples of suitable high work function metals include but are not limited to Au, Pt, indium-tin-oxide (ITO), or alloys thereof. In some embodiments, the anode layer can have a thickness in the range of about 1 nm to about 1000 nm.

The first anode sublayer 7 may comprise Al, Ag, Ni, or a combination thereof. The thickness of a first anode sublayer may vary. For example, a first anode sublayer may have thickness of about 10 nm, about 50 nm, about 70 nm, about 100 nm, or any thickness in a range defined by, or between, any of these values. In some embodiments, a first anode sublayer may have a thickness in a range of about 10 nm to about 100 nm, about 10 nm to about 70 nm, or about 40 nm to about 60 nm.

The second anode sublayer 9 may comprise Al, Ag, Au, or a combination thereof. The thickness of a second anode sublayer may also vary. For example, a second anode sublayer may have a thickness of about 25 nm, about 50 nm, about 200 nm, or any thickness in a range defined by, or between, any of these values. In some embodiments, a second anode sublayer may have a thickness in a range of about 5 nm to about 200 nm, about 10 nm to about 100 nm, or about 30 nm to about 70 nm.

In some embodiments, the first anode sublayer may comprise Al and/or the second anode sublayer may comprise Ag.

A cathode layer, e.g. cathode 35, may include a material having a lower work function than the anode layer. Examples of suitable materials for the cathode layer include those selected from alkali metals of Group 1, Group 2 metals, Group 11, Group 12, and Group 13 metals including rare earth elements, lanthanides and actinides, materials such as aluminum, indium, calcium, barium, samarium and magnesium, and combinations thereof. Li-containing organometallic compounds, LiF, and $Li_2O$ may also be deposited between the organic layer and the cathode layer to lower the operating voltage. Suitable low work function metals include but are not limited to Al, Ag, Mg, Ca, Cu, Mg/Ag, LiF/Al, CsF, CsF/Al or alloys thereof. In some embodiments, the cathode layer can have a thickness in the range of about 1 nm to about 1000 nm.

The first cathode sublayer, e.g., the layer 37, may comprise alkali metals of Group 1, Group 2 metals, Group 12 metals including rare earth elements, lanthanides and actinides, materials such as aluminum, indium, calcium, barium, samarium and magnesium, and combinations thereof. In some embodiments, the first cathode sublayer comprises Al, Ag, Au, Cu, Mg/Ag, or alloys thereof.

The thickness of a first cathode sublayer, e.g., the layer 37, may also vary. For example, a second cathode sublayer may have a thickness of about 0.1 nm, about 1 nm, about 2 nm, about 4 nm, about 5 nm, about 6 nm, about 10 nm, about 12 nm, about 20 nm, about 50 nm, or any thickness in a range defined by, or between, any of these values. In some embodiments, a second cathode sublayer may have a thickness in a range of about 0.1 nm to about 50 nm, about 1 nm to about 20 nm, about 5 nm to about 20 nm, or about 16 nm.

The second cathode sublayer 38 may comprise alkali metals of Group 1, Group 2 metals, Group 12 metals including rare earth elements, lanthanides and actinides, materials such as aluminum, indium, calcium, barium, samarium and magnesium, and combinations thereof. In some embodiments, the second cathode sublayer comprises Mg, Ca, Mg/Ag, LiF/Al, CsF, CsF/Al or alloys thereof.

The thickness of a second cathode sublayer may vary. For example, a first cathode sublayer may have thickness of about 0.1 nm, about 1 nm, about 2 nm, about 4 nm, about 5 nm, about 6 nm, about 10 nm, about 12 nm, about 20 nm, about 50 nm, or any thickness in a range defined by, or between, any of these values. In some embodiments, the first cathode sublayer may have a thickness in a range of about 0.1 nm to about 50 nm, about 0.1 nm to about 10 nm, about 0.5 nm to about 2 nm, or about 1 nm.

In some embodiments, the first cathode sublayer comprises Mg/Ag and/or the second cathode sublayer comprises Mg. In some embodiments, the first cathode sublayer is about 16 nm thick and/or the second cathode sublayer is about 1 nm thick.

The light-emitting layer, e.g. the light-emitting layer 20, may comprise a light-emitting component, and optionally, a host. A host may comprise a compound described herein, a hole-transport material, an electron-transport material, and/or an ambipolar material. In some embodiments, the device may be configured so that holes can be transferred from the anode to the light-emitting layer. In some embodiments, the device may be configured so that electrons can be transferred from the cathode to the light-emitting layer. If present, the amount of the host in a light-emitting layer can vary. In one embodiment, the amount of a host in a light-emitting layer may be in the range of from about 1% to about 99.9% by weight of the light-emitting layer. In another embodiment, the amount of a host in a light-emitting layer may be in the range of from about 90% to about 99% by weight of the light-emitting layer. In another embodiment, the amount of a host in a light-emitting layer may be about 97% by weight of the light-emitting layer.

In some embodiments, the mass of the light-emitting component may be about 0.1% to about 10%, about 1% to about 5%, or about 3% of the mass of the light-emitting layer. In some embodiments, the light-emitting layer may be a neat light-emitting layer, meaning that the light-emitting component is about 100% by weight of the light-emitting layer, or alternatively, the light-emitting layer consists essentially of light-emitting component. The light-emitting component may be a fluorescent and/or a phosphorescent compound, including but not limited to a compound disclosed herein. In some embodiments, the light-emitting component comprises a phosphorescent material.

The thickness of the light-emitting layer may vary. In one embodiment, the light-emitting layer has a thickness in the range of from about 5 nm to about 200 nm. In another embodiment, the light-emitting layer has a thickness in the range of about 10 nm to about 150 nm.

In some embodiment, the light-emitting layer may be configured to emit white light.

The compounds and compositions described herein may be useful in an emissive layer without requiring any additional hole-transport or electron-transport materials. Thus, in some embodiments, the light-emitting layer consists essentially of an electroluminescent compound and a compound disclosed herein. In some embodiments, the light-emitting layer consists essentially of a compound disclosed herein. In some embodiments, the light-emitting layer may comprise at least one hole-transport material or electron-transport material in addition to a compound disclosed herein.

The hole-transport layer, e.g., the hole-transport layer 15, may be disposed between the anode and the light-emitting layer. The hole-transport layer may comprise at least one hole-transport material. In some embodiments, the hole-transport material comprises at least one of an aromatic-substituted amine, a carbazole, a polyvinylcarbazole (PVK), e.g. poly(9-vinylcarbazole); polyfluorene; a polyfluorene copolymer; poly(9,9-di-n-octylfluorene-alt-benzothiadiazole); poly(paraphenylene); poly[2-(5-cyano-5-methylhexyloxy)-1,4-phenylene]; a benzidine; a phenylenediamine; a phthalocyanine metal complex; a polyacetylene; a polythiophene; a triphenylamine; copper phthalocyanine; 1,1-Bis (4-bis(4-methylphenyl)aminophenyl)cyclohexane; 2,9-Dimethyl-4,7-diphenyl-1,10-phenanthroline; 3,5-Bis(4-tert-butyl-phenyl)-4-phenyl[1,2,4]triazole; 3,4,5-Triphenyl-1,2,3-triazole; 4,4',4'-tris(3-methylphenylphenylamino) triphenylamine (MTDATA); N,N'-bis(3-methylphenyl)N,N'-diphenyl-[1,1'-biphenyl]-4,4'-diamine (TPD); 4,4'-bis[N-(naphthyl)-N-phenyl-amino]biphenyl (NPB); 4,4',4''-tris (carbazol-9-yl)-triphenylamine (TCTA); 4,4'-bis[N,N'-(3-tolyl)amino]-3,3'-dimethylbiphenyl (HMTPD); 4,4'-N,N'-dicarbazole-biphenyl (CBP); 1,3-N,N-dicarbazole-benzene (mCP); Bis[4-(p,p'-ditolyl-amino)phenyl]diphenylsilane (DTASi); 2,2'-bis(4-carbazolylphenyl)-1,1'-biphenyl (4Cz-PBP); N,N'N''-1,3,5-tricarbazoloylbenzene (tCP); N,N'-bis (4-butylphenyl)-N,N'-bis(phenyl)benzidine; or the like.

The hole-injection layer, e.g. the hole-injecting layer 10, may be disposed between the light-emitting layer and the anode. Various suitable hole-injection materials that can be included in the hole-injection layer are known to those skilled in the art. Exemplary hole-injection material(s) include $MoO_3$, $V_2O_5$, $WO_3$, or an optionally substituted compound selected from the following: a polythiophene derivative such as poly(3,4-ethylenedioxythiophene (PEDOT)/polystyrene sulphonic acid (PSS), a benzidine derivative such as N,N,N', N'-tetraphenylbenzidine, poly(N,N'-bis(4-butylphenyl)-N, N'-bis(phenyl)benzidine), a triphenylamine or phenylenediamine derivative such as N,N'-bis(4-methylphenyl)-N,N'-bis(phenyl)-1,4-phenylenediamine, 4,4',4"-tris(N-(naphthylen-2-yl)-N-phenylamino)triphenylamine, an oxadiazole derivative such as 1,3-bis(5-(4-diphenylamino)phenyl-1,3,4-oxadiazol-2-yl)benzene, a polyacetylene derivative such as poly(1,2-bis-benzylthio-acetylene), and a phthalocyanine metal complex derivative such as phthalocyanine copper (CuPc). In some embodiments, hole-injection materials, while still being able to transport holes, may have a hole mobility substantially less than the hole mobility of conventional hole transport materials. A p-doped hole injecting layer, e.g. p-doped hole injection layer 12, may include a hole injecting material doped with a hole-transport material, for example a p-doped hole injecting layer may comprise $MoO_3$ doped with NPB.

An electron-transport layer, e.g., electron-transport layer 30, may be disposed between the cathode and the light-emitting layer. In some embodiments, the electron-transport layer may comprise a compound described herein. Other electron-transport materials may be included, such as 2-(4-biphenylyl)-5-(4-tert-butylphenyl)-1,3,4-oxadiazole (PBD); 1,3-bis(N,N-t-butyl-phenyl)-1,3,4-oxadiazole (OXD-7), 1,3-bis[2-(2,2'-bipyridine-6-yl)-1,3,4-oxadiazo-5-yl]benzene; 3-phenyl-4-(1'-naphthyl)-5-phenyl-1,2,4-triazole (TAZ); 2,9-dimethyl-4,7-diphenyl-phenanthroline (bathocuproine or BCP); aluminum tris(8-hydroxyquinolate) (Alq3); and 1,3,5-tris(2-N-phenylbenzimidazolyl)benzene; 1,3-bis[2-(2,2'-bipyridine-6-yl)-1,3,4-oxadiazo-5-yl]benzene (BPY-OXD); 3-phenyl-4-(1'-naphthyl)-5-phenyl-1,2,4-triazole (TAZ), 2,9-dimethyl-4,7-diphenyl-phenanthroline (bathocuproine or BCP); and 1,3,5-tris[2-N-phenylbenzimidazol-z-yl]benzene (TPBI). In some embodiments, the electron transport layer may be aluminum quinolate ($Alq_3$), phenanthroline, quinoxaline, 1,3,5-tris[N-phenylbenzimidazol-z-yl]benzene (TPBI), or a derivative or a combination thereof.

In some embodiments, the light-emitting device can include an electron injection layer, e.g. electron injecting layer 25, between the cathode layer and the light-emitting layer. In some embodiments, the lowest unoccupied molecular orbital (LUMO) energy level of the electron injection material(s) is high enough to prevent it from receiving an electron from the light-emitting layer. In other embodiments, the energy difference between the LUMO of the electron injection material(s) and the work function of the cathode layer is small enough to allow the electron injection layer to efficiently inject electrons into the light-emitting layer from the cathode. A number of suitable electron injection materials are known to those skilled in the art. Examples of suitable electron injection material(s) include but are not limited to, an optionally substituted compound selected from the following: LiF, CsF, Cs doped into electron transport material as described above or a derivative or a combination thereof.

The substrate 1 may be any material, such as a glass or a metal, upon which the light-emitting diode may be mounted.

A heat dissipation layer, e.g., the heat dissipation layer 3, includes any layer of material that may be capable of increasing the surface area of the device for thermal exchange, spreading the heat uniformly throughout the device area, transferring the heat to the heat sink materials, and/or releasing the heat outside of the device. A typical heat dissipation layer may include, but is not limited to: an aluminum sheet with a fin structure, aluminum tape with thermal conductive adhesive, a copper thin film, a graphite sheet, a stainless steel film, a Si-wafer, a thin film of boron nitride, a thermal conductive grease, a gel, or combinations of above.

A capping layer, e.g., the capping layer 40, may be any layer that enhances the emission of light from an OLED device. An enhancement layer may comprise any material that is capable of increasing the emission of light by an OLED device. Examples of such materials may include, but are not limited to, transparent materials including organic small molecule materials such as NPB, TPBI, Alq3; metal oxides such as $MoO_3$, WO3, $SnO_2$ and SnO; wide band gap semiconductor compounds; etc. Additional examples include enhancement layers and/or porous films as described in co-pending patent application, entitled, "Formation of high efficient porous nano-structured light outcoupling film for organic light emitting diodes and the use of the same" (Ser. No. 61/449,032, filed 3 Mar. 2011), which is incorporated by reference in its entirety, herein.

If desired, additional layers may be included in the light-emitting device. These additional layers may include a hole-blocking layer (HBL) and/or an exciton-blocking layer (EBL). In addition to separate layers, some of these materials may be combined into a single layer.

In some embodiments, the device can include a hole-blocking layer, e.g., between the cathode and the light-emitting layer. Various suitable hole-blocking materials that can be included in the hole-blocking layer are known to those skilled in the art. Suitable hole-blocking material(s) include but are not limited to, an optionally substituted compound selected from the following: bathocuproine (BCP), 3,4,5-triphenyl-1,2,4-triazole, 3,5-bis(4-tert-butyl-phenyl)-4-phenyl-[1,2,4] triazole, 2,9-dimethyl-4,7-diphenyl-1,10-phenanthroline, and 1,1-bis(4-bis(4-methylphenyl)aminophenyl)-cyclohexane.

In some embodiments, the light-emitting device can include an exciton-blocking layer, e.g., between the light-emitting layer and the anode. In an embodiment, the band gap of the material(s) that comprise an exciton-blocking layer may be large enough to substantially prevent the diffusion of excitons. A number of suitable exciton-blocking materials that can be included in an exciton-blocking layer are known to those skilled in the art. Examples of material(s) that can compose an exciton-blocking layer include an optionally substituted compound selected from the following: aluminum quinolate ($Alq_3$), 4,4'-bis[N-(naphthyl)-N-phenyl-amino]biphenyl (NPB), 4,4'-N,N'-dicarbazole-biphenyl (CBP), and bathocuproine (BCP), and any other material(s) that have a large enough band gap to substantially prevent the diffusion of excitons.

Light-emitting devices comprising the compounds disclosed herein can be fabricated using techniques known in the art, as informed by the guidance provided herein. For example, a glass substrate can be coated with a high work functioning metal such as ITO which can act as an anode. After patterning the anode layer, a light-emitting layer that includes at least a compound disclosed herein, and an optional electroluminescent compound, can be deposited on the anode. The cathode layer, comprising a low work functioning metal (e.g., Mg:Ag), can then be deposited, e.g., vapor evaporated, onto the light-emitting layer. If desired, the device can also include an electron-transport/injection layer, a hole-blocking layer, a hole-injection layer, an exciton-blocking layer and/or a second light-emitting layer that can be added to the device using techniques known in the art, as informed by the guidance provided herein.

In some embodiments, the light-emitting device (e.g., OLED) may be configured by a wet process such as a process that comprises at least one of spraying, spin coating, drop casting, inkjet printing, screen printing, etc. Some embodiments provide a composition which may be a liquid suitable for deposition onto a substrate. The liquid may be a single phase, or may comprise one or more additional solid or liquid phases dispersed in it. The liquid typically comprises a light-emitting compound, a host material disclosed herein and a solvent.

Phototherapy

The devices disclosed herein may be useful in phototherapy. Typically, phototherapy involves exposing at least a portion of the tissue of a mammal with light, such as light from a device described herein.

The phototherapy may have a therapeutic effect, such as the diagnosis, cure, mitigation, treatment, or prevention of disease, or otherwise affecting the structure or function of the body of man or other animals. Some examples of conditions that phototherapy may be useful to treat or diagnose include, but are not limited to, infection, cancer/tumors, cardiovascular conditions, dermatological conditions, a condition affecting the eye, obesity, pain or inflammation, conditions related to immune response, etc.

Examples of infections may include microbial infection such as bacterial infection, viral infection, fungus infection, protozoa infection, etc.

Exemplary cancer or tumor tissues include vascular endothelial tissue, an abnormal vascular wall of a tumor, a solid tumor, a tumor of a head, a tumor of the brain, a tumor of a neck, a tumor of a gastrointestinal tract, a tumor of a liver, a tumor of a breast, a tumor of a prostate, a tumor of a lung, a nonsolid tumor, malignant cells of one of a hematopoietic tissue and a lymphoid tissue, lesions in a vascular system, a diseased bone marrow, diseased cells in which the disease may be one of an autoimmune and an inflammatory disease, etc.

Examples of cardiovascular conditions may include myocardial infarction, stroke, lesions in a vascular system, such as atherosclerotic lesions, arteriovenous malformations, aneurysms, venous lesions, etc. For example, a target vascular tissue may be destroyed by cutting off circulation to the desired location.

Examples of dermatological conditions may include hair loss, hair growth, acne, psoriasis, wrinkles, discoloration, skin cancer, rosacea, etc.

Examples of eye conditions may include age related macular degeneration (AMD), glaucoma, diabetic retinopathy, neovascular disease, pathological myopia, ocular histoplasmosis, etc.

Examples of pain or inflammation include arthritis, carpal tunnel, metatarsalgia, plantar fasciitis, TMJ, pain or inflammation affecting an elbow, an ankle, a hip, a hand, etc. Examples of conditions related to immune response may include HIV or other autoimmune disease, organ transplant rejection, etc.

Other non-limiting uses of phototherapy may include treating benign prostate hyperplasia, treating conditions affecting adipose tissue, wound healing, inhibiting cell growth, and preserving donated blood.

The light itself may be at least partially responsible for the therapeutic effects of the phototherapy, thus phototherapy may be carried out without a photosensitive compound. In embodiments where a photosensitive compound is not used, light in the red range (approximately 630 nm to 700 nm) may decrease inflammation in injured tissue, increase ATP production, and otherwise stimulate beneficial cellular activity.

In some embodiments, where a photosensitive compound is not used, light in the red range (approximately 600 nm to 700 nm) can be used in combination with wound dressings to effect accelerated wound healing. The wound dressing may include a hydrocolloid particles or material, for example as described in US 20080311178 (Ishikura, Jun, et al, filed Jun. 4, 2008); a transparent film, for example as described in U.S. Pat. No. 7,678,959 issued Mar. 16, 2010 to Okadam Katshiro, et al.; and/or an adhesive material. An adhesive may be any conventional adhesive and may have sufficient strength to keep the wound dressing or device in contact with a patient while not having too much strength such that wound dressing cannot be removed from the patient.

In some embodiments, at least a portion of a wound dressing is exposed to light from a device. The wound dressing may be applied to the wound of a mammal to effect accelerated healing. The dressing may be exposed to the light prior to and/or subsequent to application of the dressing to the wound site. Light in the red range may also be used in conjunction with light of other spectral wavelengths, for example blue or yellow, to facilitate post operative healing. Facial rejuvenation may be effected by applying about 633 nm radiation to the desired tissue for about 20 minutes. In some embodiments, facial skin rejuvenation is believed to be attained by applying light in the red range for a therapeutically effective amount of time.

The light may also be used in conjunction with a photosensitive compound. The photosensitive compound may be administered directly or indirectly to body tissue so that the photosensitive compound is in or on the tissue. At least a portion of the photosensitive compound may then be activated by exposing at least a portion of tissue with light.

For example, a photosensitive compound may be administered systemically by ingestion or injection, topically applying the compound to a specific treatment site on a patient's body, or by some other method. This may be followed by illumination of the treatment site with light having a wavelength or waveband corresponding to a characteristic absorption waveband of the photosensitive compound, such as about 500 or about 600 nm to about 800 nm or about 1100 nm, which activates the photosensitive compound. Activating the photosensitive compound may cause singlet oxygen radicals and other reactive species to be generated, which may lead to a number of biological effects that may destroy the tissue which has absorbed the photosensitive compound such as abnormal or diseased tissue.

The photosensitive compound may be any compound, or pharmaceutically acceptable salts, prodrugs, or hydrates thereof, which may react as a direct or indirect result of absorption of ultraviolet, visible, or infrared light. In one embodiment, the photosensitive compound may react as a direct or indirect result of absorption of red light. The photosensitive compound may be a compound which is not naturally in the tissue. Alternatively, the photosensitive compound may naturally be present in the tissue, but an additional amount of the photosensitive compound may be administered to the mammal. In some embodiments, the photosensitive compound may selectively bind to one or more types of selected target cells and, when exposed to light of an appropriate waveband, may absorb the light, which may cause substances to be produced that impair or destroy the target cells.

While not limiting any embodiment, for some types of therapies, it may be helpful if the photosensitive compound has low enough toxicity so as not to cause more harm than the disease or the condition that is to be treated with the phototherapy to which it is administered, or is capable of being formulated in a composition with sufficiently low toxicity that can be administered to the animal. In some embodiments, it may also be helpful if the photodegradation products of the photosensitive compounds are nontoxic.

Some non-limiting examples of photosensitive compounds or materials may be found in Kreimer-Bimbaum, Sem. Hematol, 26:157-73, (1989), incorporated by reference herein in its entirety, and may include, but are not limited to, chlorins, e.g., Tetrahydroxylphenyl chlorin (THPC) [652 nm], bacteriochlorins [765 nm], e.g., N-Aspartyl chlorin e6 [664 nm], phthalocyanines [600-700 nm], porphyrins, e.g., hematoporphyrin [HPD][630 nm], purpurins, e.g., [1,2,4-Trihydroxyanthraquinone] Tin Etiopurpurin [660 nm], merocyanines, psoralens, benzoporphyrin derivatives (BPD), e.g., verteporfin, and porfimer sodium; and pro-drugs such as delta-aminolevulinic acid or methylaminolevulinate, which can produce photosensitive agents such as protoporphyrin IX. Other suitable photosensitive compounds may include indocyanine green (ICG) [800 nm], methylene blue [668 nm, 609 nm], toluidine blue, texaphyrins, Talaportin Sodium (mono-L-aspartyl chlorine)[664 nm], verteprofin [693 nm], which may be useful for phototherapy treatment of conditions such as age-related macular degeneration, ocular histoplasmosis, or pathologic myopia], lutetium texaphyrin [732 nm], and rostaporfin [664 nm].

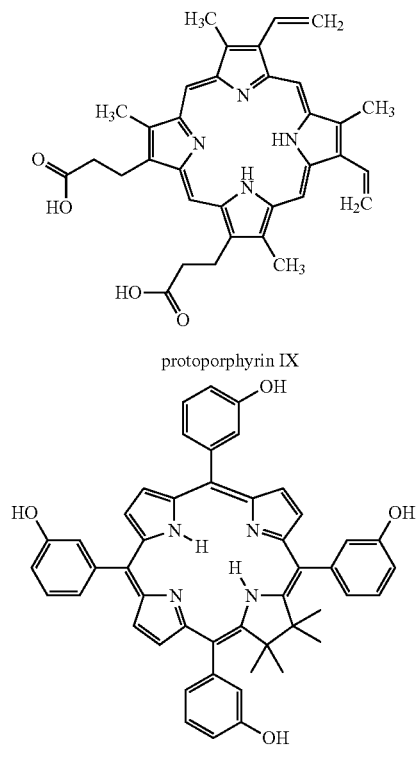

protoporphyrin IX

Tetrahydroxylphenyl chlorin (THPC)

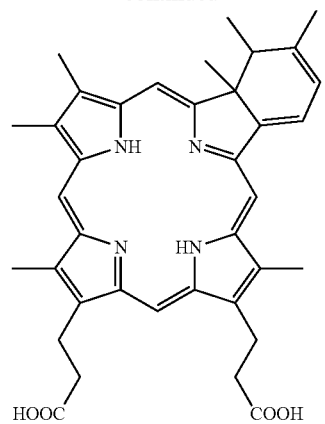

benzoporphyrin
732 nm

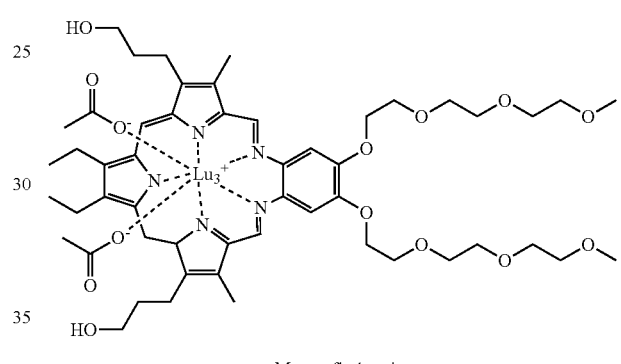

Motexafin lutetium

In some embodiments, the photosensitive compound comprises at least one component of porfimer sodium. Porfimer sodium comprises a mixture of oligomers formed by ether and ester linkages of up to eight porphorin units. The structural formula below is representative of some of the compounds present in porfimer sodium, wherein n may be 0, 1, 2, 3, 4, 5, or 6 and each R may be independently —CH(OH)CH$_3$ or —CH=CH$_2$.

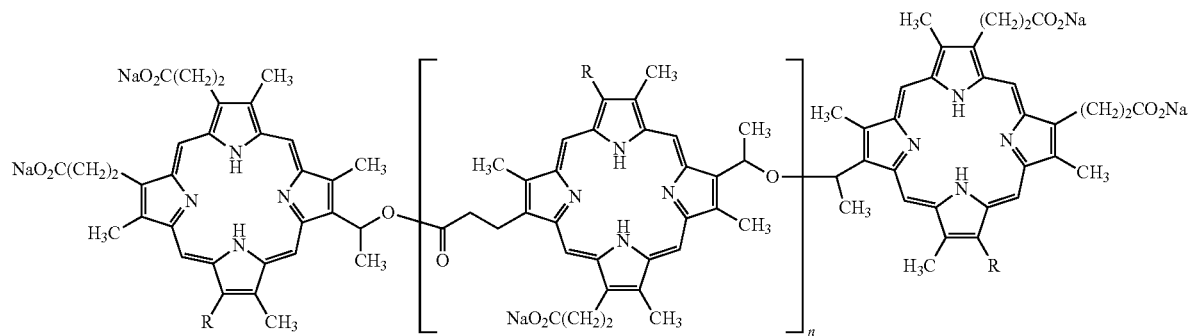

In some embodiments, the photosensitive compound may be at least one of the regioisomers of verteporphin, shown below.

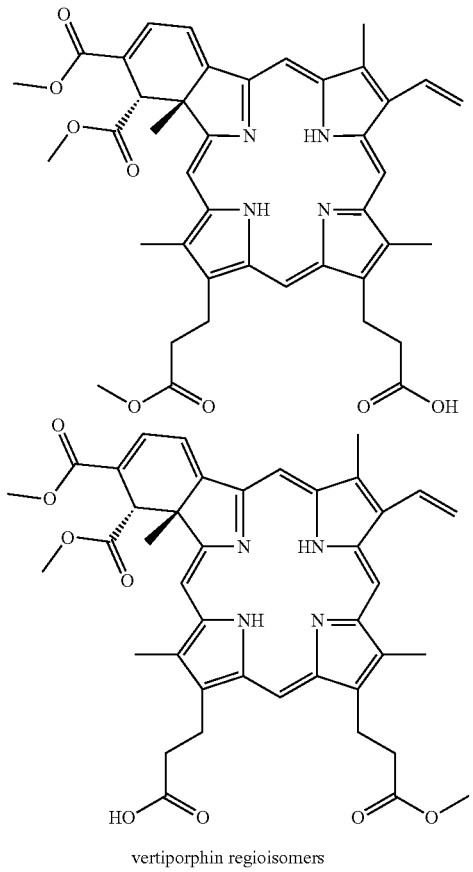

vertiporphin regioisomers

In some embodiments, the photosensitive compound may comprise a metal analogue of phthalocyanine shown below.

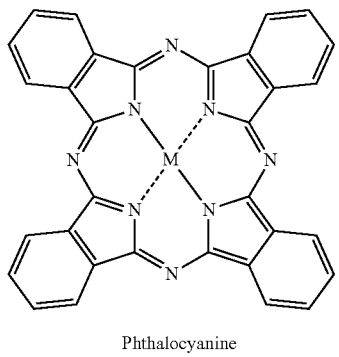

Phthalocyanine

In one embodiment, M may be zinc. In one embodiment, the compound can be zinc phthalocyanine or zinc phthalocyanine tetrasulfonate.

A photosensitive agent can be administered in a dry formulation, such as a pill, a capsule, a suppository or a patch. The photosensitive agent may also be administered in a liquid formulation, either alone, with water, or with pharmaceutically acceptable excipients, such as those disclosed in Remington's Pharmaceutical Sciences. The liquid formulation also can be a suspension or an emulsion. Liposomal or lipophilic formulations may be desirable. If suspensions or emulsions are utilized, suitable excipients may include water, saline, dextrose, glycerol, and the like. These compositions may contain minor amounts of nontoxic auxiliary substances such as wetting or emulsifying agents, antioxidants, pH buffering agents, and the like. The above described formulations may be administered by methods which may include but are not limited to intradermal, intramuscular, intraperitoneal, intravenous, subcutaneous, intranasal, epidural, oral, sublingual, intranasal, intracerebral, intravaginal, transdermal, iontophoretical, rectally, by inhalation, or topically to the desired target area, for example, the body cavity (e.g. oral, nasal, rectal), ears, nose, eyes, or skin. The preferred mode of administration may be left to the discretion of the practitioner, and may depend in part upon the site of the medical condition (such as the site of cancer or viral infection).

The dose of photosensitive agent may vary. For example, the target tissue, cells, or composition, the optimal blood level, the animal's weight, and the timing and duration of the radiation administered, may affect the amount of photosensitive agent used. Depending on the photosensitive agent used, an equivalent optimal therapeutic level may have to be empirically established. The dose may be calculated to obtain a desired blood level of the photosensitive agent, which in some embodiments may be from about 0.001 g/mL or 0.01 µg/ml to about 100 µg/ml or about 1000 µg/ml.

In some embodiments, about 0.05 mg/kg or about 1 mg/kg to about 50 mg/kg or about 100 mg/kg may be administered to the mammal. Alternatively, for topical application, about 0.15 mg/m$^2$ or about 5 mg/m$^2$ to about 30 mg/m$^2$ or about 50 mg/m$^2$ may be administered to the surface of the tissue.

The light may be administered by an external or an internal light source, such as a light-emitting device (e.g., OLED) as described herein. The intensity of radiation or light used to treat the target cell or target tissue may vary. In some embodiments, the intensity may be in the range of about 0.1 mW/cm$^2$ to about 100 mW/cm$^2$, about 1 mW/cm$^2$ to about 50 mW/cm$^2$, or about 3 mW/cm$^2$ to about 30 mW/cm$^2$. The duration of radiation or light exposure administered to a subject may vary. In some embodiments the exposure ranges from about 1 minute, about 60 minutes, or about 2 hours to about 24 hours, about 48 hours, or about 72 hours.

A certain amount of light energy may be required to provide a therapeutic effect. For example, a certain amount of light energy may be required to activate the photosensitive compounds. This may be accomplished by using a higher power light source, which may provide the needed energy in a shorter period of time, or a lower power light source may be used for a longer period of time. Thus, a longer exposure to the light may allow a lower power light source to be used, while a higher power light source may allow the treatment to be done in a shorter time. In some embodiments, the total fluence or light energy administered during a treatment may be in the range of about 5 Joules to about 1,000 Joules, about 20 Joules to about 750 Joules, or about 50 Joules to about 500 Joules. In some embodiments, the light energy administered during a treatment may depend upon the amount of tissue exposed to the light energy. For example, the light dose may be in the range of about 5 Joules/cm$^2$ to about 1,000 Joules/ cm², about 20 Joules/cm² to about 750 Joules/cm², about 30 Joules/cm² to about 1,000 Joules/cm², about 30 Joules/cm² to about 60 Joules/cm², 50 Joules/cm² to 500 Joules/cm²; or may be about 5 Joules/cm², about 15 Joules/cm², about 20 Joules/cm², about 30 Joules/cm², about 45 Joules/cm², about 50 Joules/cm², about 60 Joules/cm², about 500 Joules/cm², about 750 Joules/cm², about 1,000 Joules/cm², or any light dose in a range bounded by, or between, any of these values.

FIG. 1 is a schematic of some embodiments which further include a controller 110 and processor 120 electrically connected to an organic light-emitting diode 100 (OLED), which may help to provide a uniform power supply to facilitate homogeneous light exposure of the tissue. In some embodiments, the apparatus may further include an optional detector 140, such as photodiode, which may detect a portion of the light 160 emitted from the OLED 100, to help determine the amount of light being emitted by the OLED 100. For example, the detector 140 may communicate a signal related to the intensity of the light 160 received from the OLED 100 to the processor 120, which, based upon the signal received, may communicate any desired power output information to the controller 100. Thus, these embodiments may provide real time feedback which allows the control of the intensity of light emitted from the OLED 100. The detector 140 and the processor 120 may be powered by compact power supply, such as a battery pack 130, or by some other power source.

In some embodiments related to phototherapy, the LED device may further comprise a dosage component. A dosage component may be configured to control the device to provide a sufficient amount of light to activate a sufficient portion of a photosensitive compound to provide a therapeutic effect for treating a disease, or if no photosensitive compound is used, to control the device to provide a sufficient amount of light to achieve a therapeutic effect in a person or animal, e.g., a mammal. For example, a dosage component may comprise a timer that is configured to control delivery of light from the device for an amount of time sufficient to deliver the appropriate light dosage. The timer may automatically stop the emission from the device once the appropriate light dosage has been delivered. The dosage component may also comprise a positioning component that positions the device so that emitted light is delivered to the appropriate area of a mammal body and is at an appropriate distance from the affected tissue to deliver an effective amount of light. The dosage component may be configured to work with a particular photosensitive compound, or may provide flexibility. For example, a physician, a veterinarian, or another appropriate medical practitioner may set the parameters of the dosage component for use by a patient outside of the practitioner's office, such as at the patient's home. In some embodiments, the device may be provided with a set of parameters for various photosensitive compounds to assist a medical practitioner in configuring the device.

In some embodiments, the device may further include a wireless transmitter electrically connected to an component of the apparatus generating treatment information, e.g., level of intensity, time of application, dosage amount, to communicate/transfer data to another external receiving device, like cell phone, PDA or to doctor's office. In some embodiments, the apparatus may further include an adhesive tape which may be used to attach the apparatus on the tissue surface so as to stabilize it on the target area.

For phototherapy and other applications, a wavelength convertor may be positioned in the device to receive at least a portion of light emitted from the organic light-emitting diode in a lower wavelength range, such as about 350 nm to less than about 600 nm, and convert at least a portion of the light received to light in a higher wavelength range, such as about 600 nm to about 800 nm. The wavelength convertor may be a powder, a film, a plate, or in some other form and, may comprise: yttrium aluminum garnet (YAG), alumina ($Al_2O_3$), yttria ($Y_2O_3$), titania ($TiO_2$), and the like. In some embodiments, the wavelength convertor may comprise at least one dopant which is an atom or an ion of an element such as Cr, Ce, Gd, La, Tb, Pr, Sm, Eu, etc.

In some embodiments, translucent ceramic phosphor may be represented by a formula such as, but not limited to $(A_{1-x}E_x)_3D_5O_{12}$, $(Y_{1-x}E_x)_3D_5O_{12}$; $(Gd_{1-x}E_x)_3D_5O_{12}$; $(La_{1-x}E_x)_3D_5O_{12}$; $(Lu_{1-x}E_x)_3D_5O_{12}$; $(Tb_{1-x}E_x)_3D_5O_{12}$; $(A_{1-x}E_x)_3Al_5O_{12}$; $(A_{1-x}E_x)_3Ga_5O_{12}$; $(A_{1-x}E_x)_3In_5O_{12}$; $(A_{1-x}Ce_x)_3D_5O_{12}$; $(A_{1-x}Eu_x)_3D_5O_{12}$; $(A_{1-x}Tb_x)_3D_5O_{12}$; $(A_{1-x}E_x)_3Nd_5O_{12}$; and the like. In some embodiments, the ceramic may comprise a garnet, such as a yttrium aluminum garnet, with a dopant. Some embodiments provide a composition represented by the formula $(Y_{1-x}Ce_x)_3Al_5O_{12}$. In any of the above formulas, A may be Y, Gd, La, Lu, Tb, or a combination thereof; D may be Al, Ga, In, or a combination thereof; E may be Ce, Eu, Tb, Nd, or a combination thereof; and x may be in the range of about 0.0001 to about 0.1, from about 0.0001 to about 0.05, or alternatively, from about 0.01 to about 0.03

SYNTHETIC EXAMPLES

The following are examples of some methods that may be used to prepare compounds described herein.

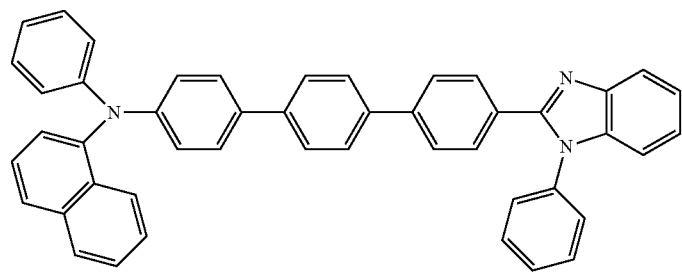

Host-1

-continued
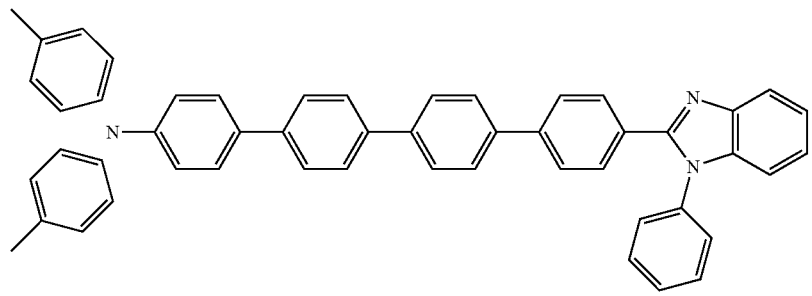
Host-3
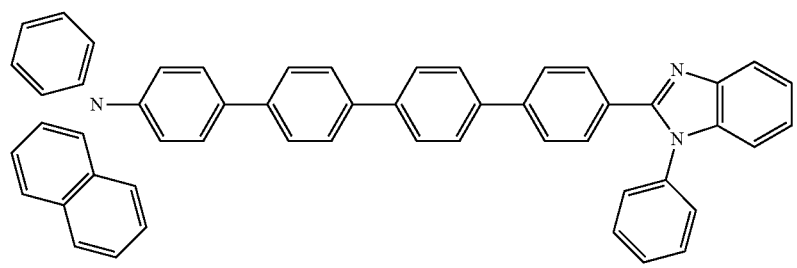
Host-2
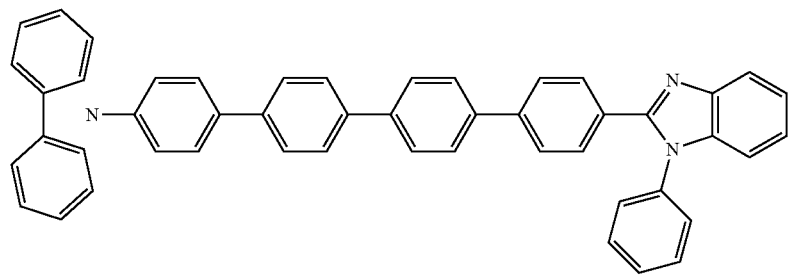
Host-4
Example 1
Organic Synthesis
Example 1.1
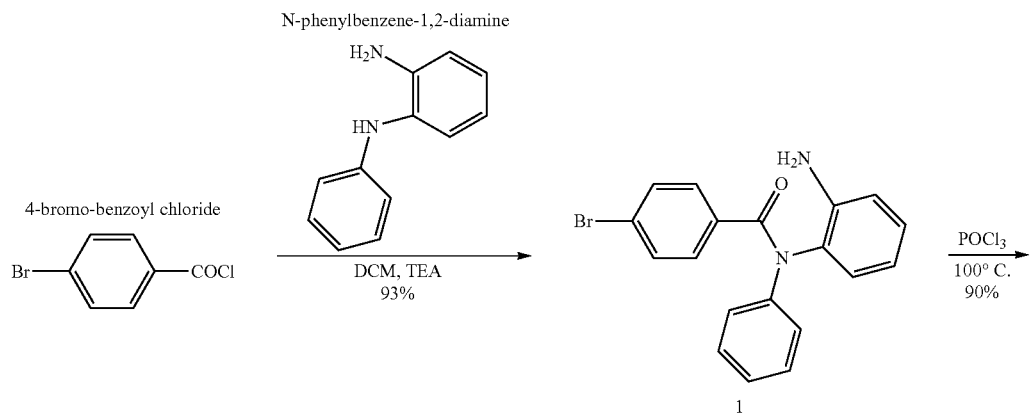

-continued

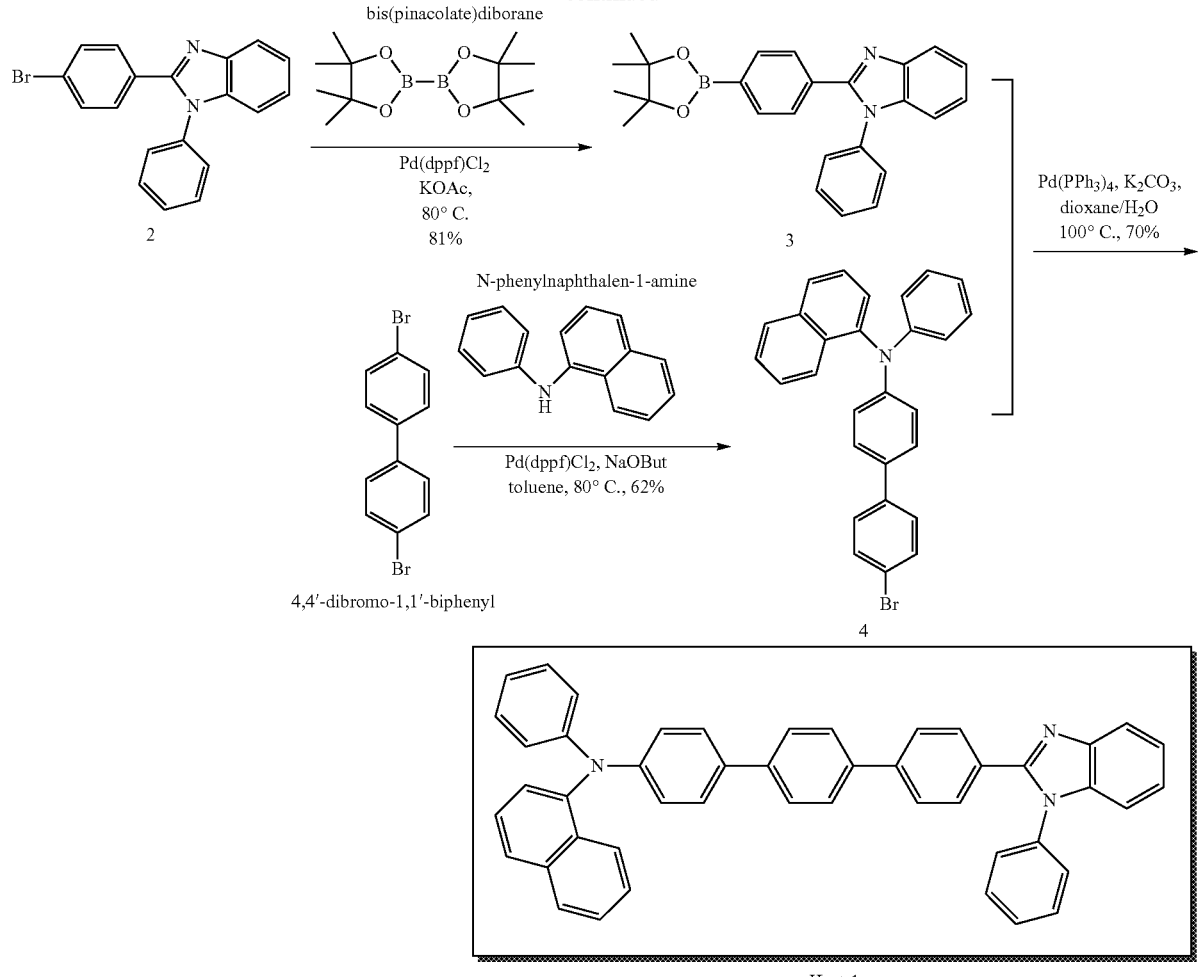

Example 1.1.1

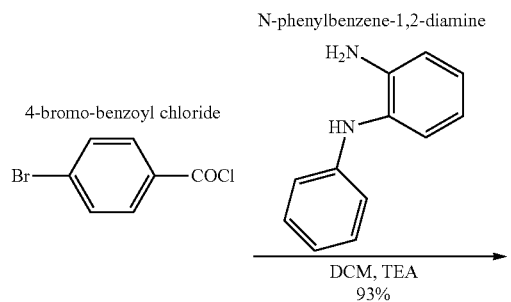

4-Bromo-N-(2-(phenylamino)phenyl)benzamide (1): To a solution of 4-bromo-benzoyl chloride (11 g, 50 mmol) in anhydrous dichloromethane (DCM) (100 ml), was added N-phenylbenzene-1,2-diamine (10.2 g, 55 mmol), then triethylamine (TEA) (17 ml, 122 mmol) slowly. The whole was stirred at room temperature (RT) overnight. Filtration gave a white solid 1 (6.5 g). The filtrate was worked up with water (300 ml), then extracted with DCM (300 ml) three times. The organic phase was collected and dried over MgSO$_4$, concentrated and recrystallized in DCM/hexanes to give another portion of white solid 1 (10.6 g). Total amount of product 1 is 17.1 g, in 93% yield.

Example 1.1.2

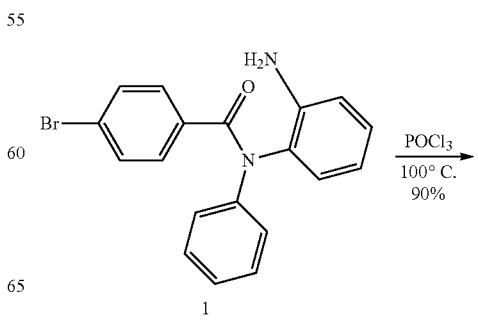

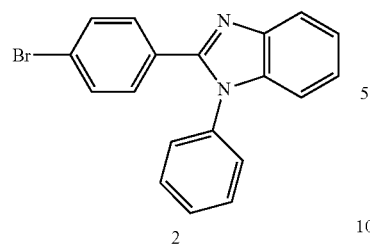

2-(4-bromophenyl)-1-phenyl-1H-benzo[d]imidazole (2): To a suspension of amide 1 (9.6 g, 26 mmol) in anhydrous 1,4-dioxane (100 mL) was added phosphorus oxychloride (POCl$_3$) (9.2 mL, 100 mmol) slowly. The whole was then heated at 100° C. overnight. After cooling to RT, the mixture was poured into ice (200 g) with stirring. Filtration, followed by recrystallization in DCM/hexanes gave a pale grey solid 2 (8.2 g, in 90% yield).

Example 1.1.3

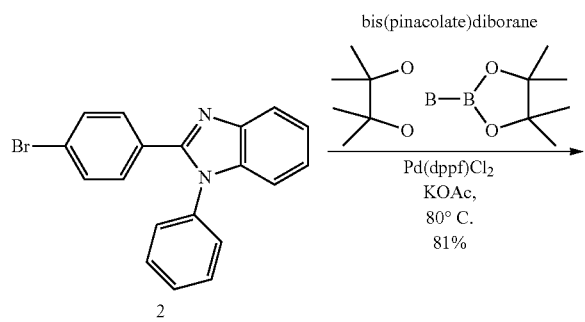

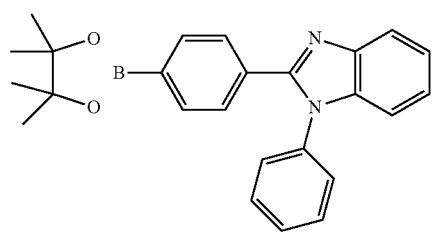

1-phenyl-2-(4-(4,4,5,5-tetramethyl-1,3,2-dioxaborolan-2-yl)phenyl)-1H-benzo[d]imidazole (3): A mixture of Compound 2 (0.70 g, 2 mmol), bis(pinacolate)diborane (0.533 g, 2.1 mmol), bis(diphenylphosphino)ferrocene]dichloropalladium (Pd(dppf)Cl$_2$) (0.060 g, 0.08 mmol) and anhydrous potassium acetate (KOAc) (0.393 g, 4 mmol) in 1,4-dioxane (20 ml) was heated at 80° C. under argon overnight. After cooling to RT, the whole was diluted with ethyl acetate (80 ml) then filtered. The solution was absorbed on silica gel, then purified by column chromatography (hexanes/ethyl acetate 5:1 to 3:1) to give a white solid 3 (0.64 g, in 81% yield).

Example 1.1.4

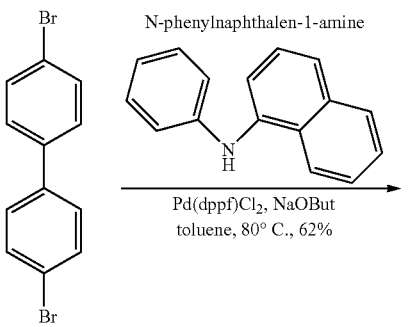

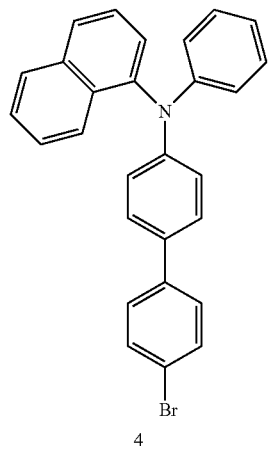

N-(4'-bromo-[1,1'-biphenyl]-4-yl)-N-phenylnaphthalen-1-amine (4): A mixture of N-phenylnaphthalen-1-amine (4.41 g, 20 mmol), 4,4'-dibromo-1,1'-biphenyl (15 g, 48 mmol), sodium tert-butoxide (4.8 g, 50 mmol) and Pd(dppf)Cl$_2$ (0.44 g, 0.6 mmol) in anhydrous toluene (100 ml) was degassed and heated at 80° C. for 10 hours. After cooling to RT, the mixture was poured into dichloromethane (400 ml) and stirred for 30 min, then washed with brine (100 ml). The organic is collected and dried over Na$_2$SO$_4$, loaded on silica gel, and purified by flash column (hexanes to hexanes/ethyl acetate 90:1) to give a solid which was washed with methanol and dried under air to give a white solid 4 (5.58 g, in 62% yield).

Example 1.1.5

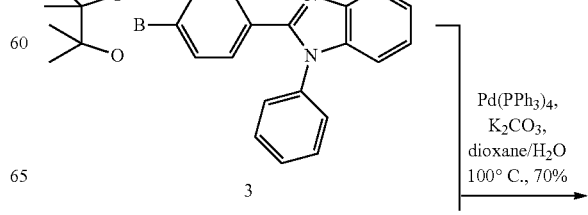

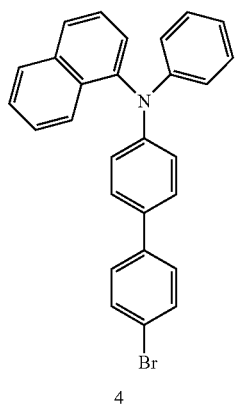

4

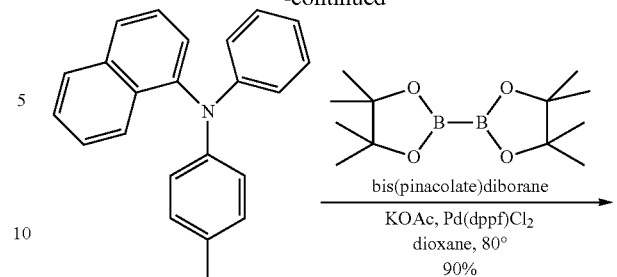

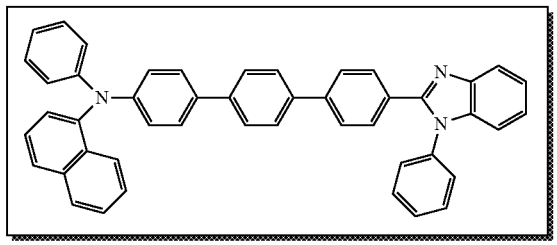

Host-1

Host-1: A mixture of compound 3 (0.80 g, 2 mmol), compound 4 (0.90, 2 mmol), tetrakis(triphenylphosphine)palladium(0) (Pd(PPh$_3$)$_4$) (0.115 g, 0.1 mmol) and potassium carbonate (0.69 g, 5 mmol) in dioxane/water (25 ml/5 ml) was degassed and heated at 100° C. overnight. After cooling down to RT, the mixture was worked up with water and ethyl acetate (150 ml×3). The organic phase was collected and dried over Na$_2$SO$_4$, loaded on silica gel, purified by flash column (hexanes/ethyl acetate 8:1 to 6:1) to give an off white solid (Host-1) (0.90 g, in 70% yield). LCMS data: calcd for C$_{47}$H$_{34}$N$_3$ (M+H)=640.3; found: m/e=640.

Example 1.2

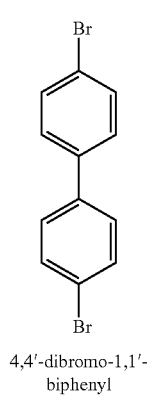

4,4′-dibromo-1,1′-biphenyl

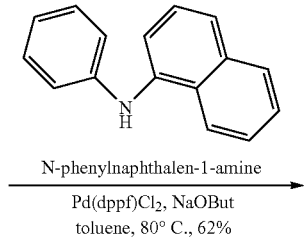

N-phenylnaphthalen-1-amine

→ Pd(dppf)Cl$_2$, NaOBut
toluene, 80° C., 62%

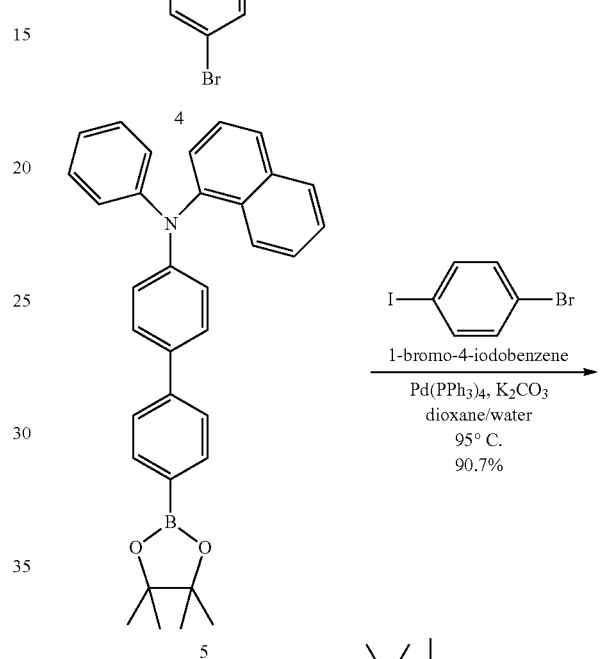

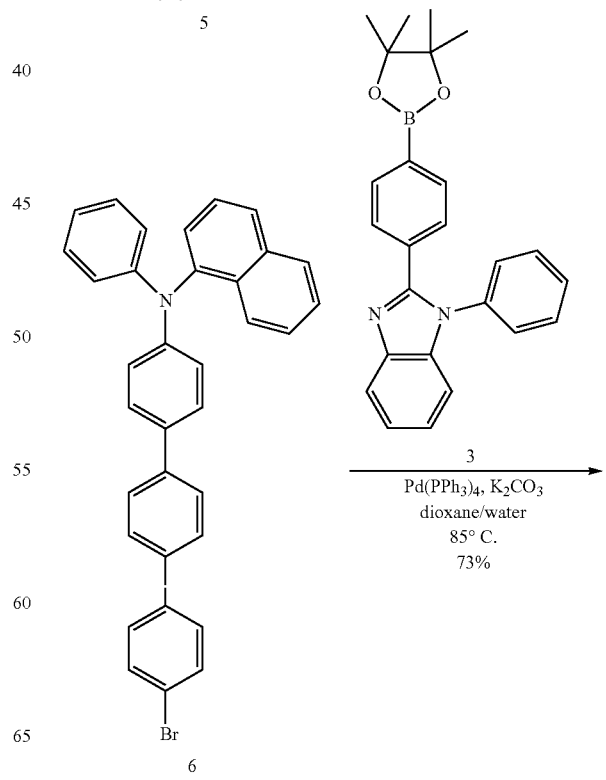

-continued

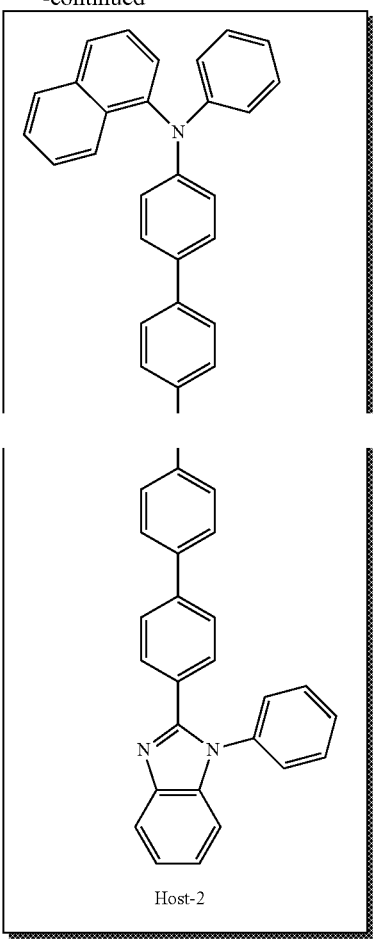

Host-2

Example 1.2.1

-continued

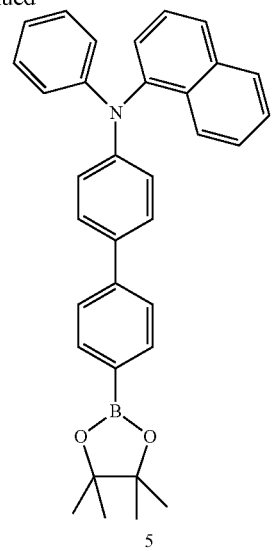

5

N-phenyl-N-(4'-(4,4,5,5-tetramethyl-1,3,2-dioxaborolan-2-yl)-[1,1'-biphenyl]-4-yl)naphthalen-1-amine (5): A mixture of Compound 4(5.5 g, 12.2 mmol), bis(pinacolate)diborane (3.10 g, 12.2 mmol), Pd(dppf)Cl$_2$ (0.446 mg, 0.6 mmol) and KOAc (5.5 g, 56 mmol) in anhydrous dioxane (60 ml) was degassed and heated at 80° C. overnight. After being cooled to RT, the mixture was poured into ethyl acetate (200 ml), washed with brine (150 ml). The organic solution was dried over Na$_2$SO$_4$, loaded on silica gel and purified by flash column (hexanes to hexanes/ethyl acetate 30:1) to collect the major fraction. After removal of solvent, the solid was washed with methanol, filtered and dried in air to give a white solid 5 (5.50 g, in 90% yield).

Example 1.2.2

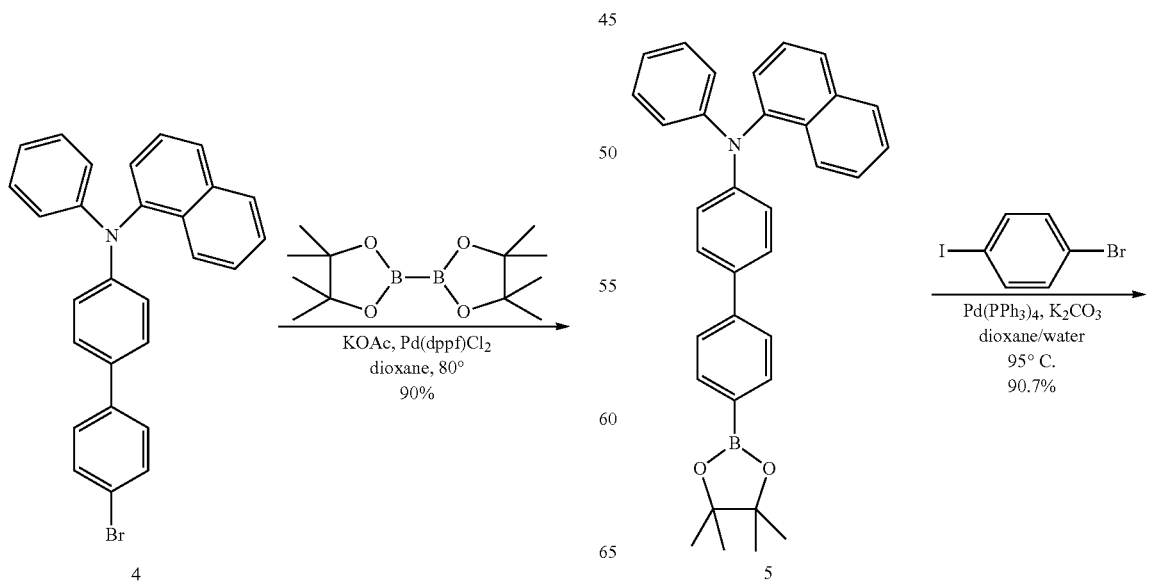

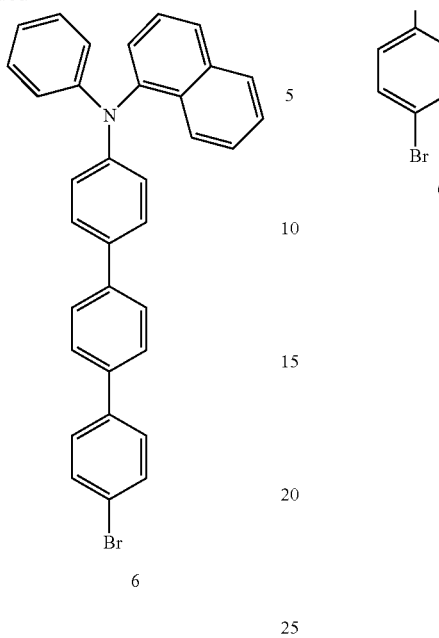

N-(4"-bromo-[1,1':4',1"-terphenyl]-4-yl)-N-phenylnaphthalen-1-amine (6): A mixture of compound 5 (4.5 g, 9.0 mmol), 1-bromo-4-iodobenzene (5.12 g, 18 mmol), Pd(PPh$_3$)$_4$ (0.52 g, 0.45 mmol) and potassium carbonate (4.436 g, 32 mmol) in dioxane/water (150 ml/30 ml) was degassed and heated at 95° C. overnight. After being cooled to RT, the mixture was poured into dichloromethane (300 ml), washed with brine, dried over Na$_2$SO$_4$, then loaded on silica gel, purified by flash column (hexanes to hexanes/ethyl acetate 20:1) to give a light yellow solid (4.30 g, in 90.7% yield).

Example 1.2.3

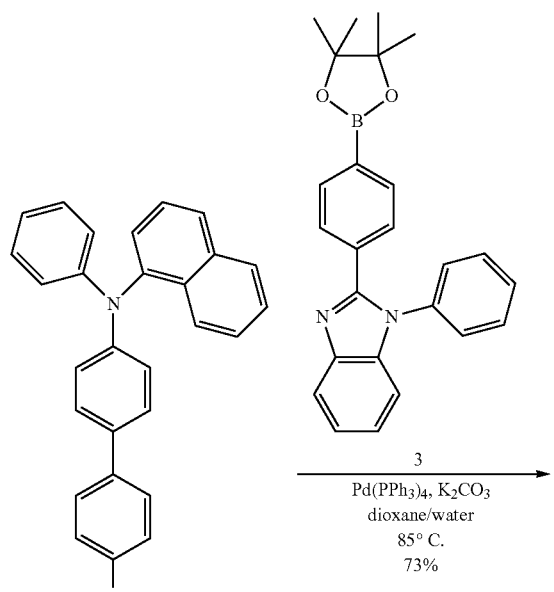

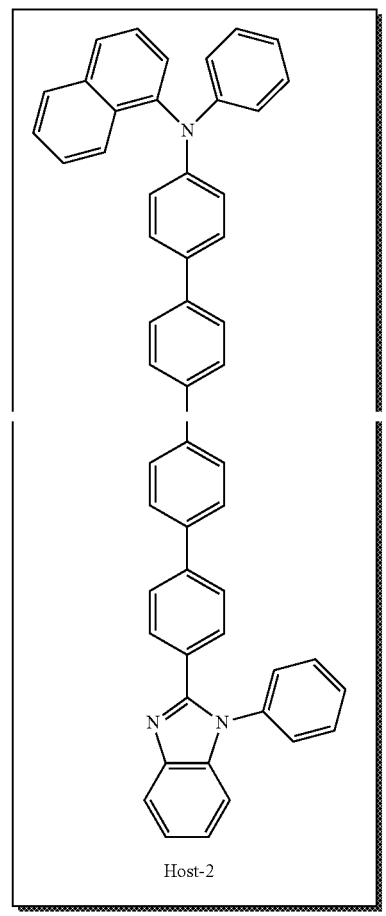

Host-2: A mixture of compound 6 (4.21 g, 8.0 mmol), compound 3 (3.166 g, 8.0 mmol), Pd(PPh$_3$)$_4$ and potassium carbonate (3.31 g, 24 mmol) in dioxane/water (150 ml/30 ml) was degassed and heated at 85° C. for 18 hours. After being cooled to RT, the mixture was filtered. The solid and the filtrate were collected separately. The filtrate was diluted with dichoromethane (250 ml) and washed with brine. The organic phase was dried over Na$_2$SO$_4$, loaded on silica gel and purified by flash column (hexanes to hexanes/ethyl acetate 10:1 to 5:1 to 4:1). The major desired blue fluorescent fraction was collected, and concentrated to give a white solid (0.55 g, with m/e=716 corresponding to the target molecular weight). The solid from the first filtration was redissolved in dichloromethane (200 ml), loaded on silica gel, and purified by flash column (hexanes to hexanes/ethyl acetate 4:1 to dichloromethane to hexanes/ethyl acetate 3:1) to collect the desired fraction, concentrated to 200 ml and kept in −10 C overnight. The white precipitate was filtered and dried in air to give a floppy white solid, Host-2 (3.65 g). The overall yield is 73%. LCMS data: calcd for C$_{53}$H$_{38}$N$_3$ (M+H): 716.3; found m/e=716.

Example 1.3
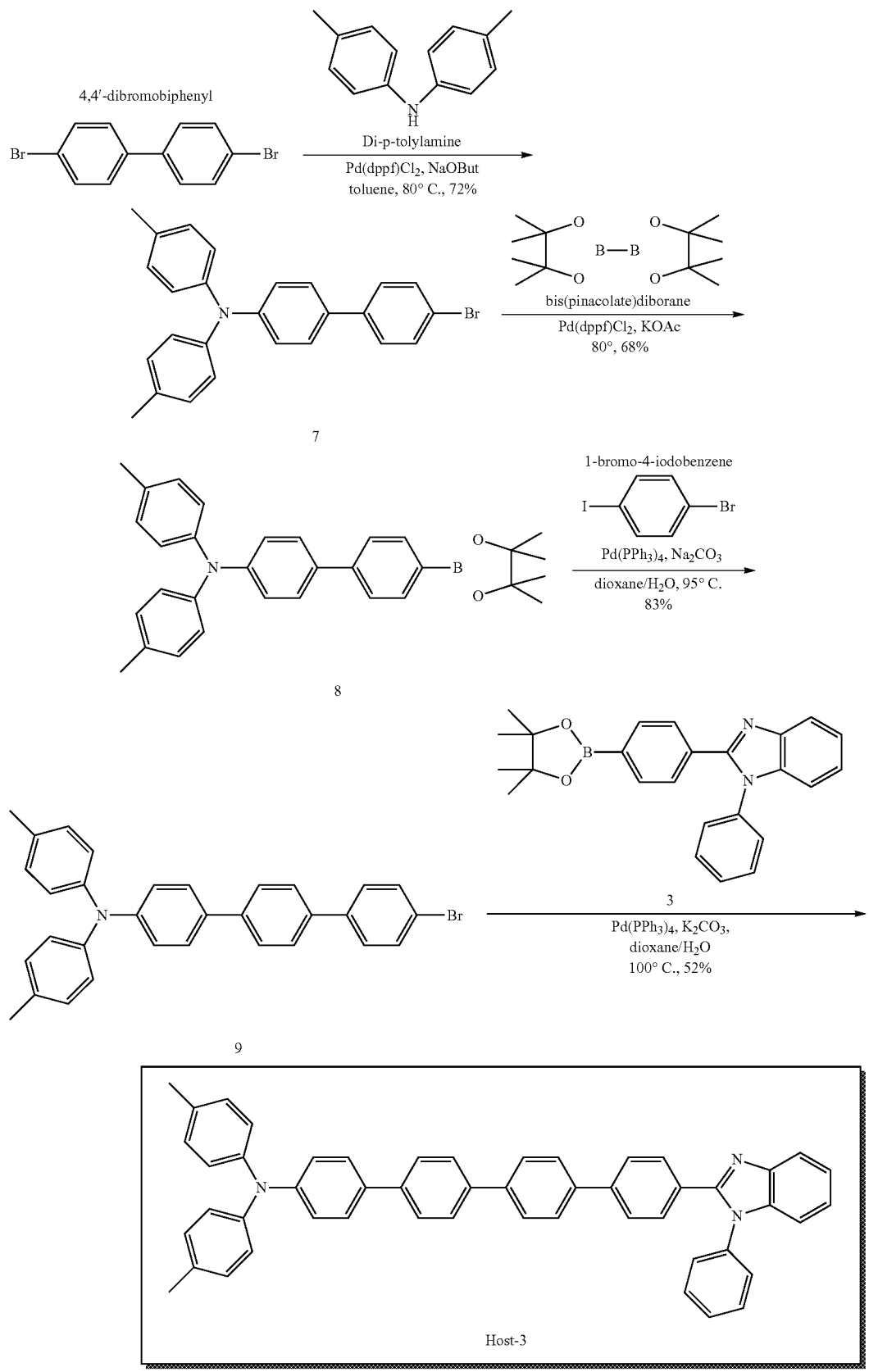
Host-3

Example 1.3.1

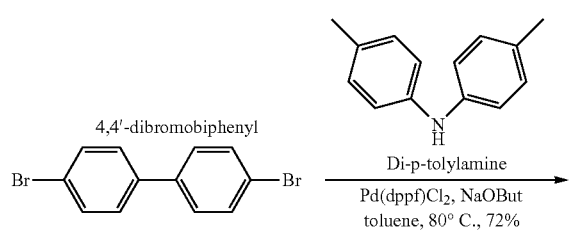

4'-bromo-N,N-dip-tolylbiphenyl-4-amine (7): Di-p-tolylamine (6.0 g, 30.4 mmol), 4,4'-dibromobiphenyl (23.7 g, 76.0 mmol), sodium tert-butoxide (7.26 g, 91.2 mmol), and [1,1-bis(diphenylphosphino)ferrocene]palladium(II)dichloride (Pd(dppf)Cl$_2$) (666 mg, 0.912 mmol, 3 mol %) were added to anhydrous toluene (about 250 ml) and degassed in argon for about 30 minutes. The resulting mixture was heated at about 80° C. for about 6 hours, after which a TLC analysis indicated that most of the di-p-tolylamine was consumed. After being cooled to RT, the mixture was poured into saturated aqueous sodium bicarbonate and extracted with 2 portions of ethyl acetate. The organic layers were pooled, washed with water and brine, then dried over MgSO$_4$. After filtration the extract was concentrated to dryness on a rotary evaporator, then loaded onto silica gel. A flash column (gradient of 100% hexane to 1% methylene chloride in hexane) resulted in 9.4 g (72%) of a white solid confirmed by $^1$H NMR in CDCl$_3$.

Example 1.3.2

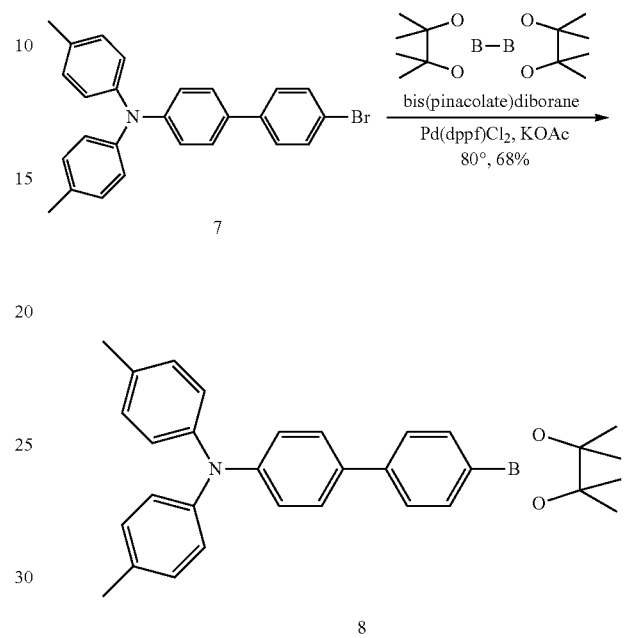

4'-(4,4,5,5-tetramethyl-1,3,2-dioxaborolan-2-yl)-N,N-di-p-tolyl-[1,1'-biphenyl]-4-amine (8): A mixture of Compound 7 (2.0 g, 4.67 mmol), bis(pinacolate)diborane (1.27 g, 5 mmol), Pd(dppf)Cl$_2$ (0.18 g, 0.25 mmol) and potassium acetate (0.98 g, 10 mmol) in anhydrous dioxane (50 ml) was degassed and heated at 80° C. for 16 hours. After being cooled to RT, the whole was poured into ethyl acetate (100 ml) and the solid ws filtered off. The organic solution was loaded on silica gel, and purified by flash column (hexanes/ethyl acetate 6:1) to give a white solid 8 (1.5 g, in 68% yield).

Example 1.3.3

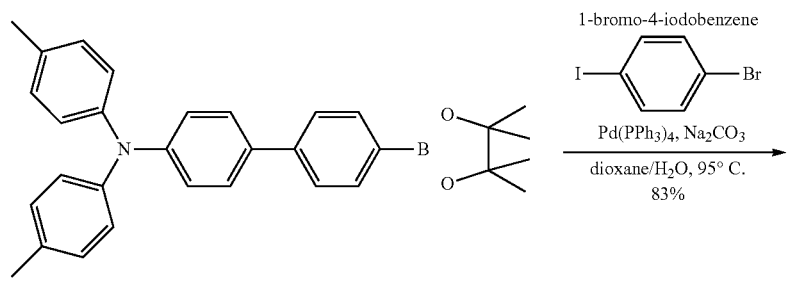

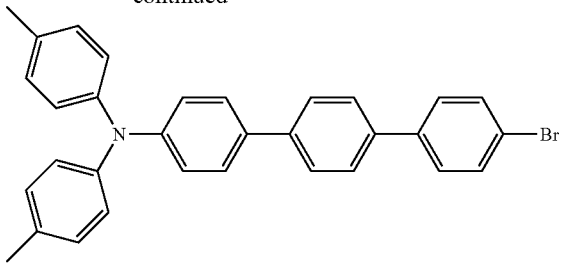

9

4"-bromo-N,N-di-p-tolyl-[1,1':4',1"-terphenyl]-4-amine (9): A mixture of compound 8 (3.0 g, 6.3 mmol), 1-bromo-4-iodobenzene (3.57 g, 12.6 mmol), Pd(PPh$_3$)$_4$ and potassium carbonate (1.74 g, 12.6 mmol) in dioxane/water (40 ml/8 ml) was degassed and heated at 95° C. for 24 hours. After being cooled to RT, a yellow solid precipitated and was collected by filtration. The solid was recrystallized in dichloromethane/methanol to give a pale yellow solid (2.22 g). The filtrate was loaded on silica gel and purified by flash column to give additional amount of yellow solid 9 (0.42 g). The total amount of solid was 2.64 g, in 83% yield.

Example 1.3.4

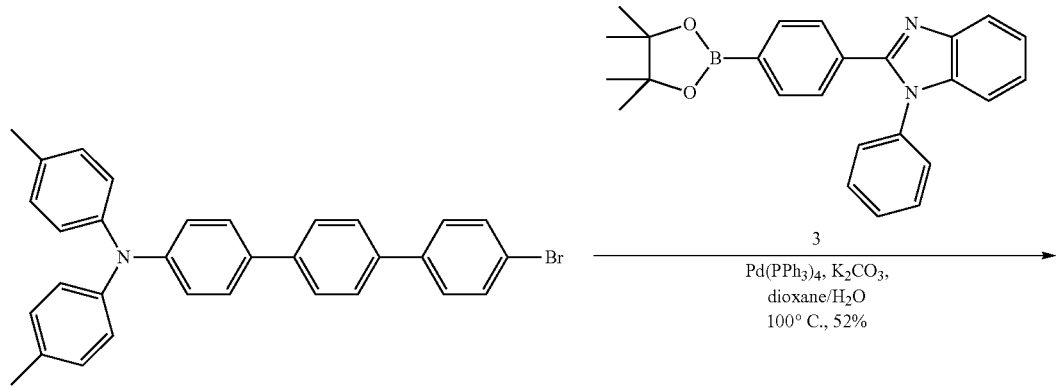

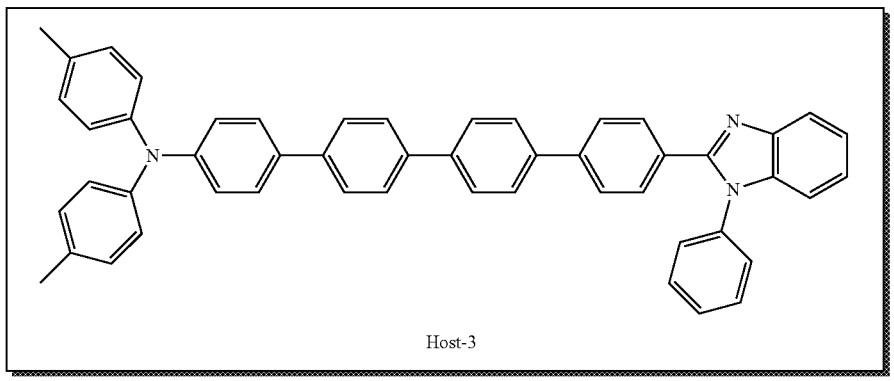

Host-3

Host-3: A mixture of Compound 9 (1.50 g, 3 mmol), Compound 3 (1.18 g, 3 mmol), Pd(PPh$_3$)$_4$ (0.173 g, 0.15 mmol) and potassium carbonate (1.38 g, 10 mmol) in dioxane/water (40 ml/11 ml) was degassed and heated at 100° C. overnight. After being cooled to RT, the mixture was poured into dichloromethane (200 ml) then washed with water (150 ml×2). The organic solution was dried over Na$_2$SO$_4$, loaded on silica gel and purified by flash column (hexanes/dichloromethane 2:1 to hexanes/ethyl acetate 9:1 to 5:1) to give a white solid Host-3 (1.1 g, in 52% yield). LCMS data: calcd for C$_{51}$H$_{40}$ON$_3$ (M+H)=694.3; found m/e=694.

Example 1.4
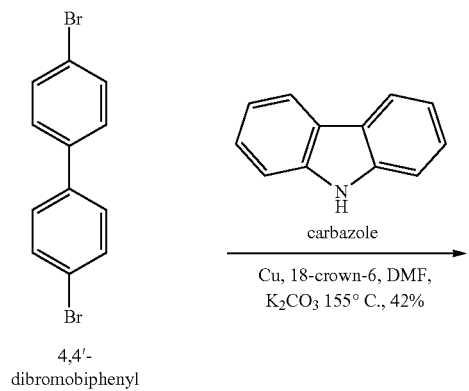
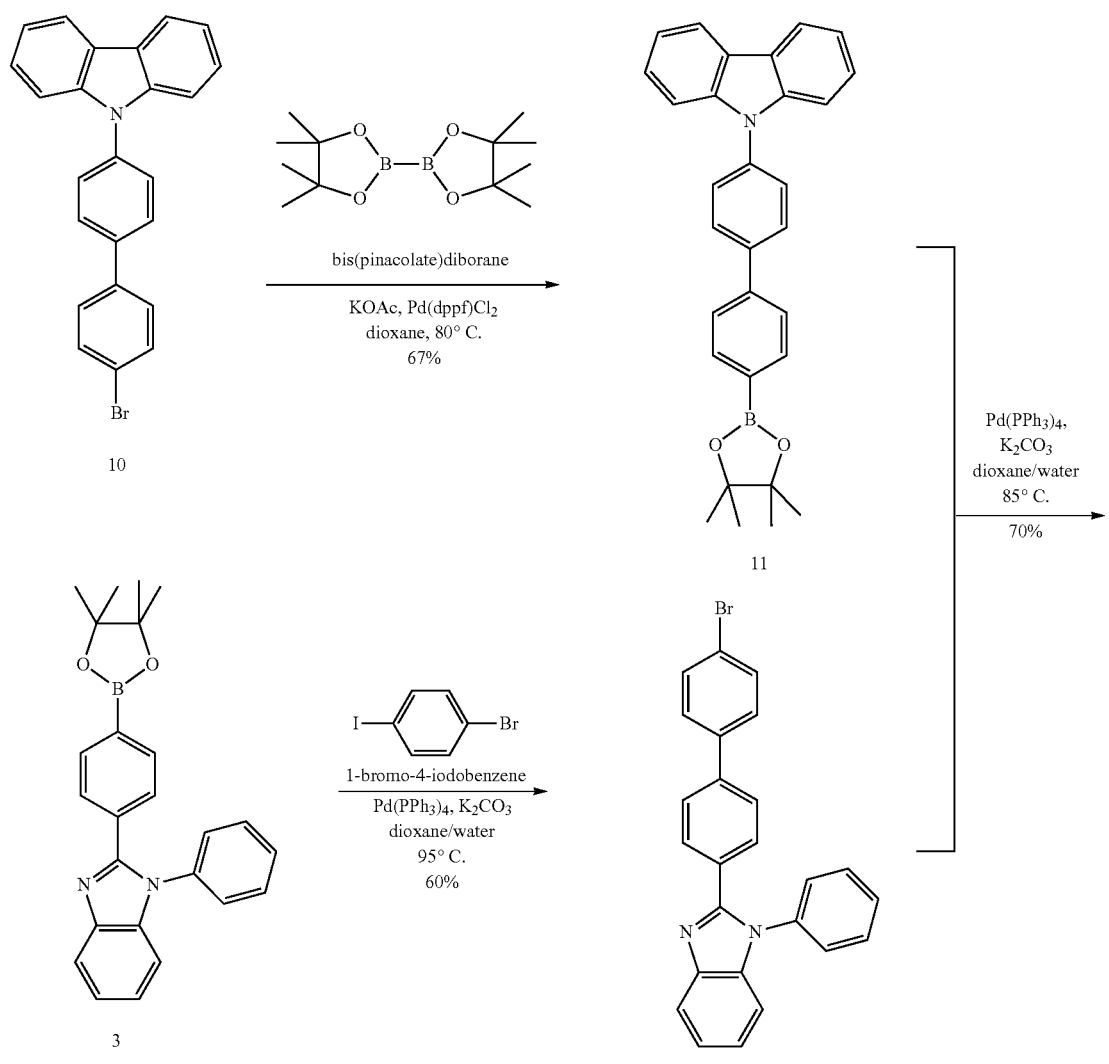

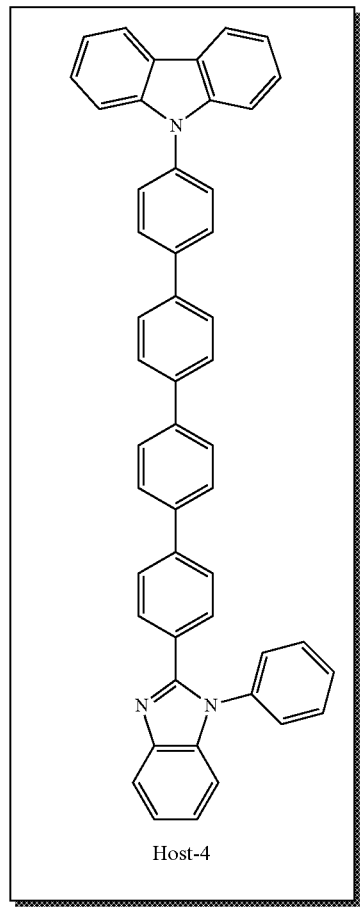

Host-4

9-(4'-bromobiphenyl-4-yl)-9H-carbazole (10): A mixture of carbazole (300 mg, 1.81 mmol), 4,4'-dibromobiphenyl (846 mg, 2.71 mmol), copper (344 mg, 5.43 mmol), 18-crown-6 (187 mg, 0.71 mmol), potassium carbonate (750 mg, 5.43 mmol), and anhydrous N,N-dimethylformamide (10 ml) was degassed for 30 minutes. The mixture was heated at about 155° C. for 66 hours under argon. After being cooled to RT, the mixture was poured into methylene chloride (400 ml) and the subsequent mixture was filtered. The filtrate was loaded on silica gel. A flash column (silica, 10% methylene chloride in hexane) and reprecipitation in methylene chloride/hexanes yielded 304 mg (42% yield) of pure product 10; confirmed by HNMR.

Example 1.4.1

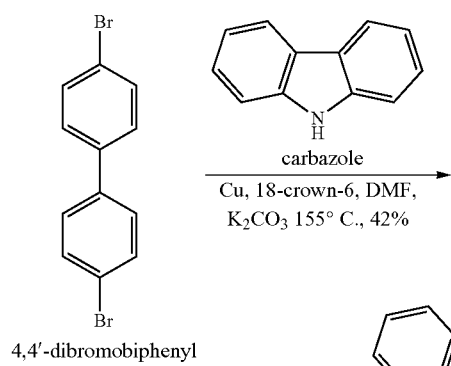

Example 1.4.2

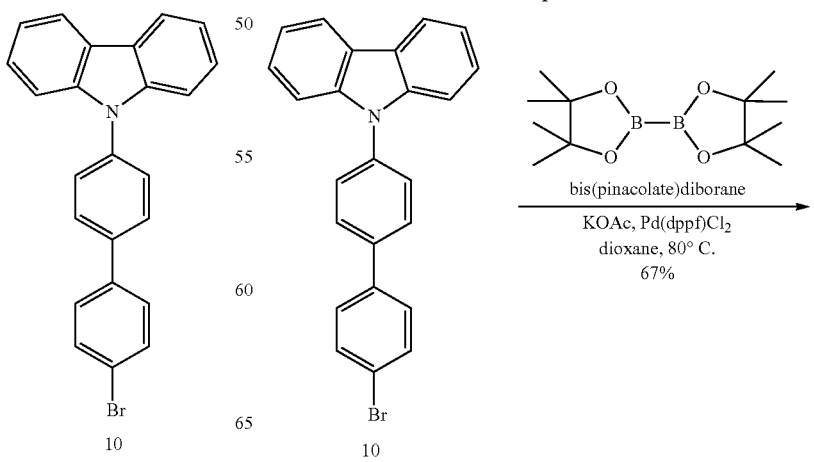

-continued

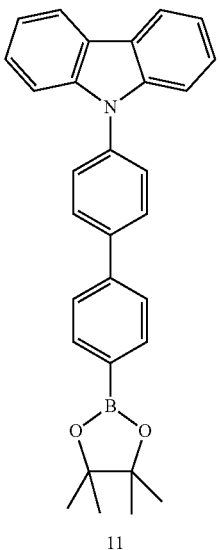

11

9-(4'-(4,4,5,5-tetramethyl-1,3,2-dioxaborolan-2-yl)-[1,1'-biphenyl]-4-yl)-9H-carbazole (11): A mixture of compound 10 (2.0 g, 5.02 mmol), bis(pinacolate)diborane (1.276 g, 5.02 mmol), Pd(dppf)Cl$_2$ (150 mg, 0.20 mmol) and potassium acetate (4.0 g, 41 mmol) in anhydrous dioxane (50 ml) was degassed and heated at 80° C. overnight. After being cooled to RT, the mixture was poured into brine, and extracted with ethyl acetate (200 ml). The organic phase was collected and dried over Na$_2$SO$_4$, then loaded on silica gel, purified by flash column (hexanes to hexanes/dichloromethane 5:1 to hexanes/ethyl acetate 8:1) to afford a white solid 11 (1.50 g, in 67% yield).

-continued

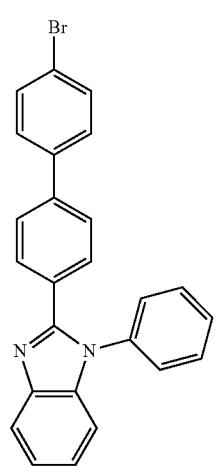

12

2-(4'-bromo-[1,1'-biphenyl]-4-yl)-1-phenyl-1H-benzo[d]imidazole (12): A mixture of compound 3 (4.01 g, 10.1 mmol), 1-bromo-4-iodobenzene (5.73 g, 20.2 mmol), Pd(PPh$_3$)$_4$ (0.58 g, 0.5 mmol) and potassium carbonate (4.2 g, 30 mmol) in dioxane/water (60 ml/10 ml) was degassed and heated at 95° C. overnight. After being cooled to RT, the mixture was filtered to collect the precipitate, which was redissolved in hot dichloromethane. The dichloromethane solution was filtered and concentrated with presence of methanol until a large amount of white precipitate forms. Filtration and drying in air gave a white solid (2.58 g, in 60% yield).

Example 1.4.4

Example 1.4.3

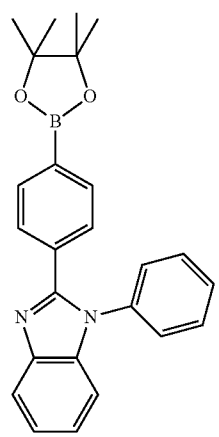

3

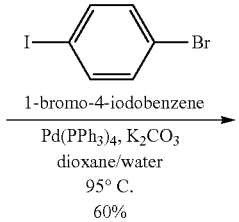

1-bromo-4-iodobenzene
Pd(PPh$_3$)$_4$, K$_2$CO$_3$
dioxane/water
95° C.
60%

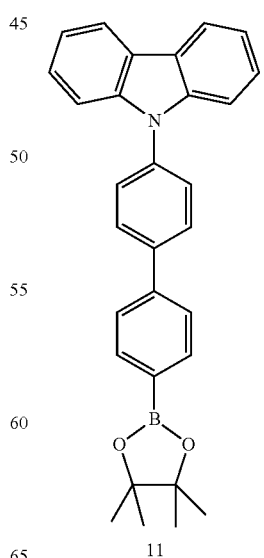

11

Pd(PPh$_3$)$_4$,
K$_2$CO$_3$
dioxane/water
85° C.
70%

43

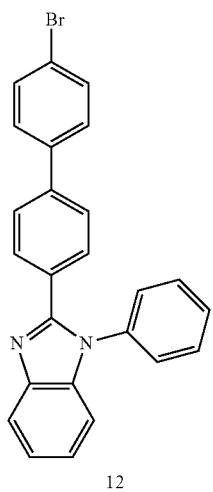

12

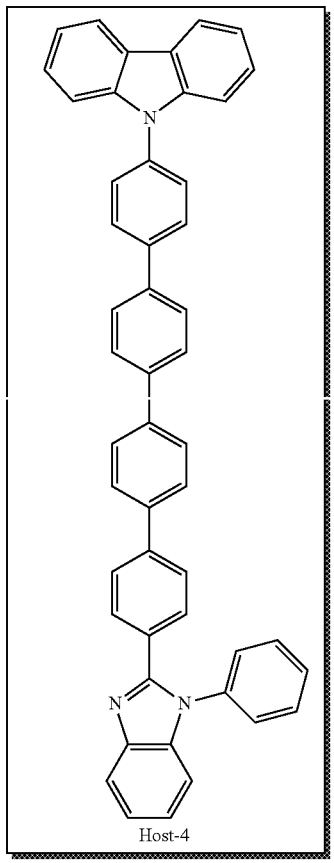

Host-4

Host-4: A mixture of compound 11 (1.34 g, 3.01 mmol), compound 12 (1.28 g, 3.01 mmol), tetrakis(triphenylphosphine)palladium(0) (Pd(PPh$_3$)$_4$) (0.173 g, 0.15 mmol) and potassium carbonate (1.38 g, 10 mmol) in dioxane/water (80 ml/16 ml) was degassed and heated at 85° C. overnight. After being cooled to RT, the mixture was poured into dichoromethane (30 ml), then washed twice with brine. The organic phase was collected and concentrated to cause precipitation. The suspension was filtered and the solid and the filtrate were collected separately and loaded on silica gel and purified by flash column (dichloromethane to dichloromethane/ethyl acetate 10:1) to give white solid Host-4 (1.40 g, in 70% overall yield). LCMS data: calcd for C$_{49}$H$_{34}$N$_3$ (M+H): 664.3; found: m/e=664.

44

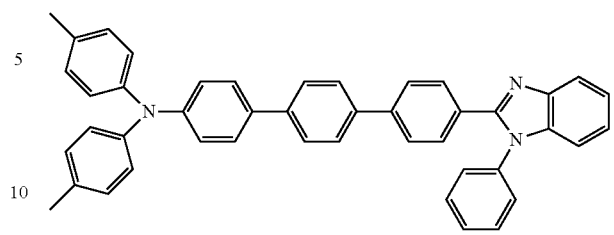

Compound X

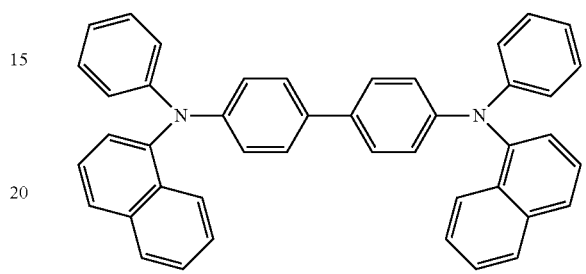

Compound Y

"NPB"

Example 2

OLED Device Configuration and Performance

An example of a configuration of a device comprising a compound described herein is shown in FIG. 2. Such a device comprises the following layers in the order given: an ITO anode 5, a PEDOT hole-injection layer 10, an NPB hole-transport layer 15, a first light-emitting layer 20, a TPBI electron-transport and hole-blocking layer 30, and a LiF/Al cathode 35.

For these particular examples, the ITO anode 5 was about 150 nm thick; the PEDOT hole injection layer 10 was about 30 nm thick; the NPB hole-transport layer 15 was about 40 nm thick; the light-emitting layer 20 was about 30 nm thick; the TPBI electron transport and hole blocking layer 30 was about 30 nm thick; the LiF sublayer (not shown) of the cathode 35 was about 0.5 nm thick; and the Al sublayer of the cathode (not shown) was about 120 nm thick. The device was then encapsulated with a getter attached glass cap to cover the emissive area of the OLED device in order to protect from moisture, oxidation or mechanical damage. Each individual device had an area of about 12 mm$^2$.

Fabrication of Light-Emitting Devices:

The ITO substrates having sheet resistance of about 14 ohm/sq were cleaned ultrasonically and sequentially in detergent, water, acetone and then IPA; and then dried in an oven at 80° C. for about 30 min under ambient environment. Substrates were then baked at about 200° C. for about 1 hour in an ambient environment, then under UV-ozone treatment for about 30 minutes. PEDOT:PSS (hole-injection material) was then spin-coated on the annealed substrate at about 4000 rpm for about 30 sec. The coated layer was then baked at about 100° C. for 30 min in an ambient environment, followed by baking at 200° C. for 30 min inside a glove box (N$_2$ environment). The substrate was then transferred into a vacuum chamber, where 4,4'-bis[N-(naphthyl)-N-phenyl-amino]biphenyl (NPB) [hole transporting material]) was vacuum deposited at a rate of about 0.1 nm/s rate under a base pressure of about 2×10$^{-7}$ torr. Bis(1-phenylisoquinoline)(acetylacetonate)iridium (III) ("Ir(piq)$_2$acac") (10 wt %) was co-deposited as an emissive layer with Host-2 material at about 0.01 nm/s and about 0.10 nm/s, respectively, to make the appropriate thickness ratio.

For some devices, Ir(PQ)$_2$acac was used as the emitter, co-deposited with host material in 6 wt % doping concentration. The deposition rate of emitter and host were 0.006 nm/s and 0.1 nm/s, respectively. The host materials were, for example, Host-1, Host-2, etc. 1,3,5-Tris(1-phenyl-1H-benzimidazol-)$_2$-yl)benzene (TPBI) was then deposited at about 0.1 nm/s rate on the emissive layer. A layer of lithium fluoride (LiF) (electron injection material) was deposited at about 0.005 nm/s rate followed by deposition of the cathode as Aluminum (Al) at about 0.3 nm/s rate.

The following devices were prepared according to the general procedure above with varying host and emitters:

TABLE 1

| Device | Host | Emitter/Concentration |
| --- | --- | --- |
| A | Host-2 | Ir(piq)$_2$acac/10 wt % |
| B | Host-2 | Ir(piq)$_2$acac/6 wt % |
| C | Host-2 | Ir(PQ)$_2$acac/6 wt % |

Device C

Device C fabricated with the same configuration as Device A or Device B, but with different emitting complex as Ir(PQ)$_2$acac, which emits peak wavelength at 600 nm. The turn-on voltage for the device was about 2.5 volts The EQE (external quantum efficiency), luminous efficiency and power efficiency of the device at 1000 cd/m$^2$ were about 16.2%, 30.3 cd/A and 26.6 lm/w for Host-2 as the host (Device C) and EQE=15.4%, LE=27.8 cd/A, PE=24 lm/w for device with Host-1 as the host.

Figure 7:
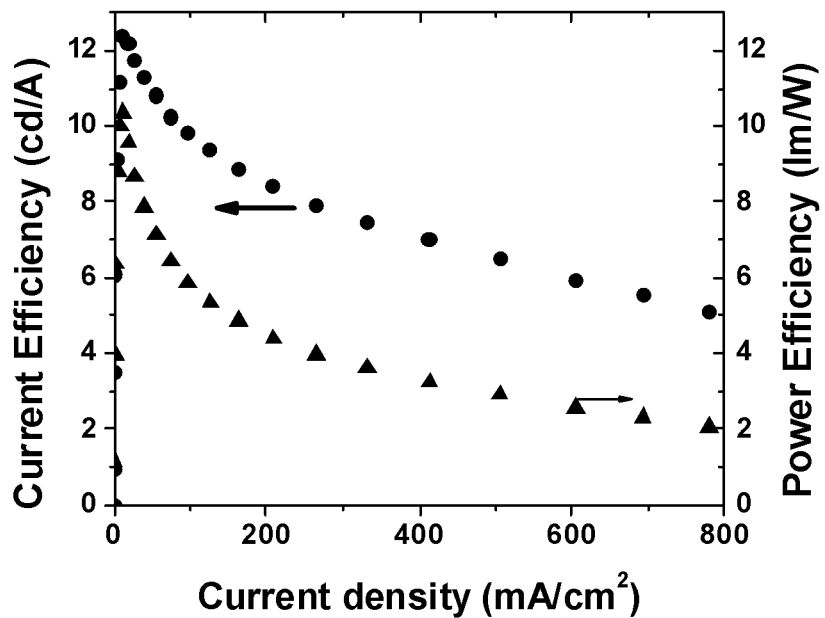
FIG. 7 is a plot of current efficiency/power efficiency vs. current density of an embodiment of a light-emitting device.
Figure 8:
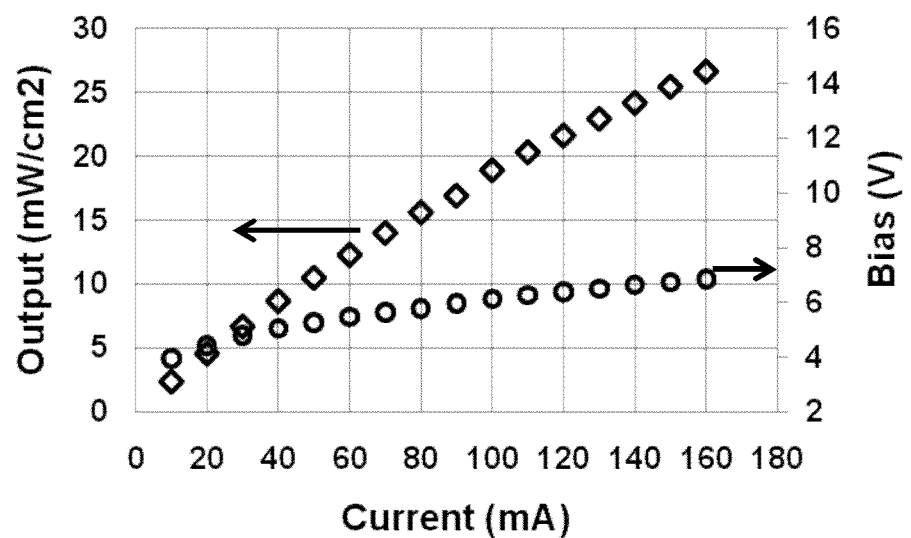
FIG. 8 is a plot of power output/voltage vs. current of an embodiment of a light-emitting device.

EL spectra was measured with a Spectrascan spectroradiometer PR-670 (Photo Research, Inc., Chatsworth, Calif., USA); and I-V-L characteristics were taken with a Keithley 2612 SourceMeter (Keithley Instruments, Inc., Cleveland, Ohio, USA) and PR-670. In addition, device performance of the device was evaluated by measuring the current density and luminance as a function of the driving voltage, as shown in FIG. 3-6. The turn-on voltage for the device was about 2.5 volts and the maximum luminance was about 39,700 cd/m$^2$ with 12 mm$^2$ area device at about 8V. The EQE (external quantum efficiency), luminous efficiency and power efficiency of the device at 1000 cd/m$^2$ were about 15.5%, 12.3 cd/A and 10.4 lm/w at 630 nm emission. For ex-vivo efficacy study with tumor cell a large area device (Area=1.6 cm2), Device A, was fabricated, whose output power (mW/cm2) is shown in FIG. 7.

Device D

A device may be fabricated in a manner similar to the following. The substrate (glass-SiON/Metal foil) was cleaned ultrasonically and sequentially in detergent, water, acetone and then IPA; and then dried in an oven at about 80° C. for about 30 min under ambient environment. Substrate was then baked at about 200° C. for about 1 hour under ambient environment, then under UV-ozone treatment for about 30 minutes. Soon after UV-ozone treatment, substrates were loaded into a deposition chamber. A bi-layer reflective type bottom anode, e.g., Al (about 50 nm) and Ag (about 40 nm) were deposited sequentially at a rate of about 0.1 nm/s. Molybdenum oxide (MoO$_3$, about 10 nm) was deposited as a hole-injecting layer. MoO$_3$ was co-deposited with NPB with a ratio of about 5 wt % to about 95 wt % (about 20 nm) as a p-doping type hole-injecting layer. NPB (about 20 nm) was then deposited as a hole-transport layer. Bis(1-phenylisoquinoline)(acetylacetonate)iridium (III) ("Ir(piq)$_2$acac") (10 wt %) was co-deposited as an emissive layer with Host-2 material at about 0.01 nm/s and about 0.10 nm/s, respectively, to make the appropriate thickness ratio and a total thickness of about 30 nm. 1,3,5-Tris(1-phenyl-1H-benzimidazol-)$_2$-yl)benzene (TPBI, about 30 nm) was then deposited at about 0.1 nm/s rate on the emissive layer. A thin layer of lithium fluoride (LiF, about 1 nm) (electron-injecting material) was deposited at about 0.005 nm/s rate, followed by deposition of the magnesium (Mg, about 1 nm) at about 0.005 nm/s rate. A semi-transparent cathode (about 16 nm) was deposited by co-deposition of magnesium (Mg) and silver (Ag) at a ratio of about 1:3 by weight. Finally a capping layer as NPB (about 60 nm) was deposited to enhance light output by micro cavity effect. All the deposition was done at a base pressure of about 2×10$^{-7}$ torr. Referring to FIG. 3, the first anode sublayer 7 was Al (about 50 nm thick), the second anode sublayer 9 was Ag (about 40 nm thick), the hole-injecting layer 10 was MoO$_3$ (about 10 nm thick), the p-doped hole-injecting layer 12 was MoO$_3$:NPB (about 20 nm thick), the hole-transport layer 15 was NPB (about 20 nm thick), the light-emitting layer 20 was Host-2: Ir(piq)$_2$acac (about 30 nm thick), the electron-transport layer 30 was TPBI (about 30 nm thick), the electron-injecting layer 25 was LiF (about 1 nm thick), the second cathode sublayer 38 was Mg (about 1 nm thick), the first cathode sublayer 37 was Mg:Ag (about 16 nm thick), and the capping layer 40 was NPB (about 60 nm thick). The device was then encapsulated with a getter attached clear glass cap to cover the emissive area of the OLED device in order to protect from moisture, oxidation or mechanical damage. In order to minimize heat effect for such large area device, a thermal compensating layer was attached on the backside of the substrate with heat sink. This layer was a typical Al heat sink with fin structure. Other materials such as Cu-film and alloy films can also be used for similar purpose depending on the thermal conductivity of the materials. Each individual device has an area of about 1.8 cm$^2$.

Figure 9:
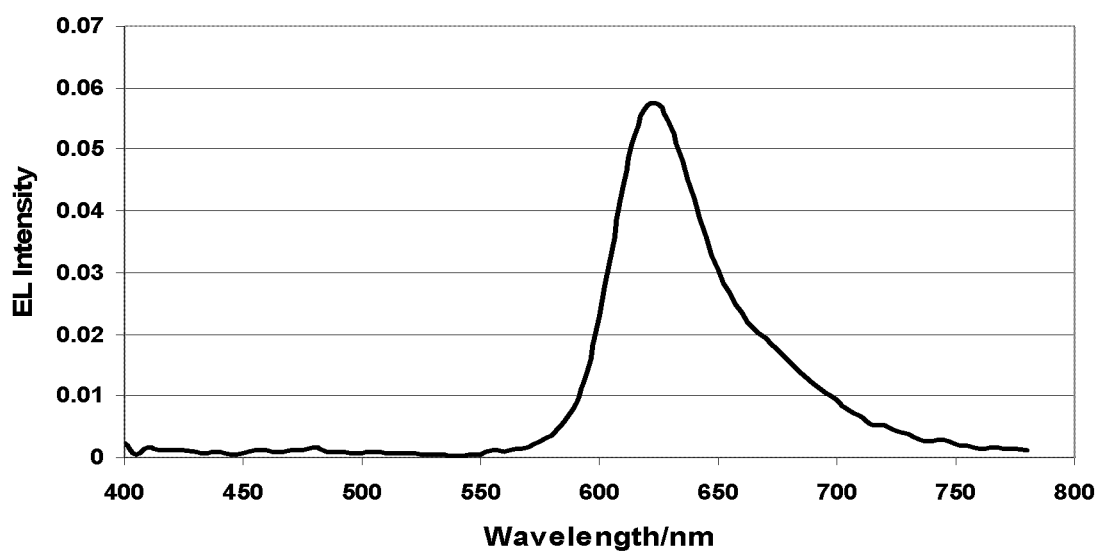
FIG. 9 is the electroluminescence spectrum of an embodiment of a light-emitting device.
Figure 10:
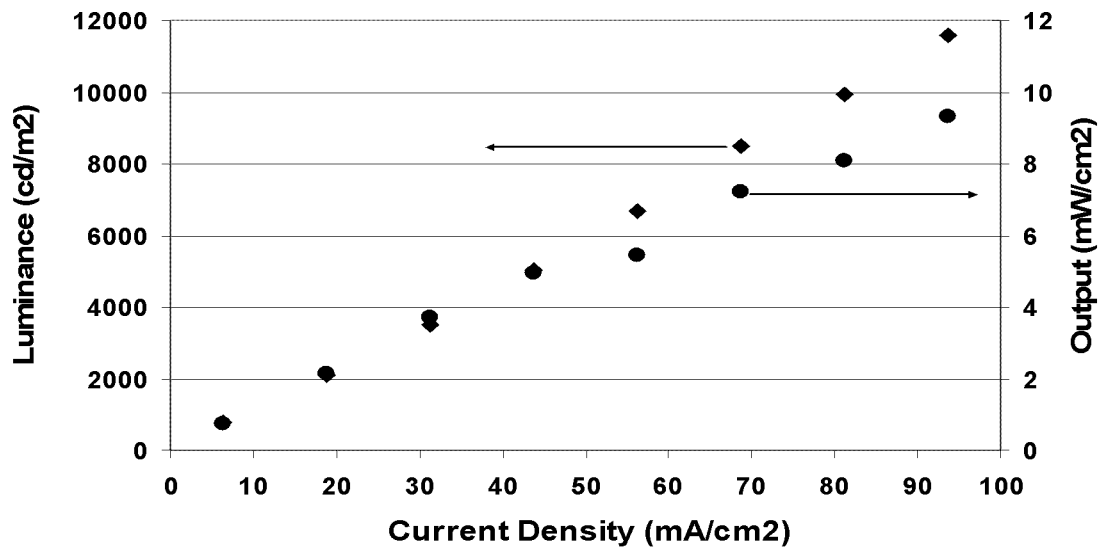
FIG. 10 is a plot of luminance and light power output as a function of current density.
Figure 11:
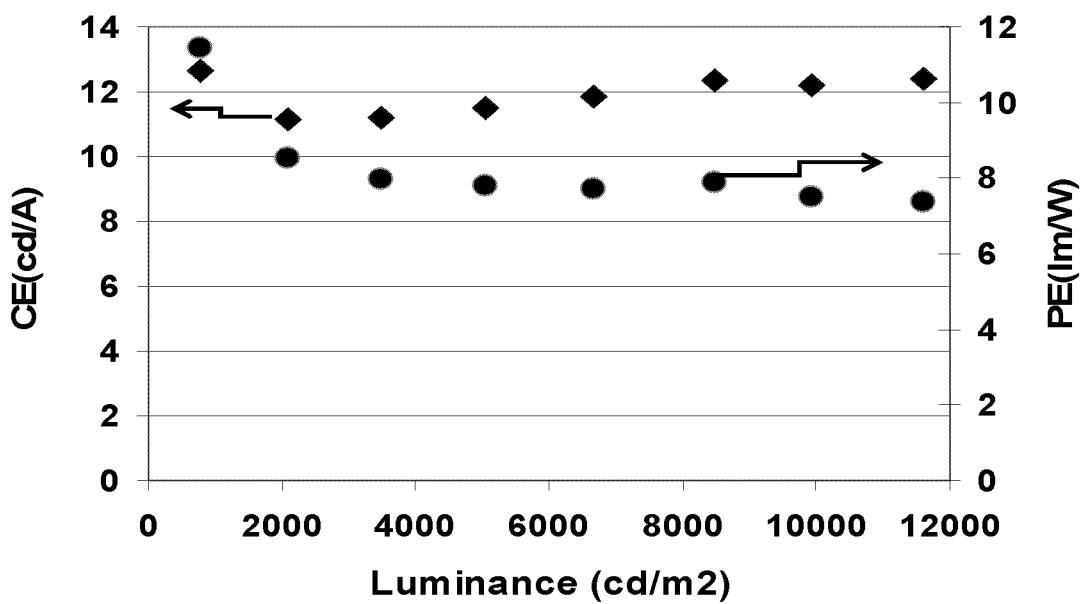
FIG. 11 is a plot of current efficiency and power efficiency as a function of luminance.
Figure 12:
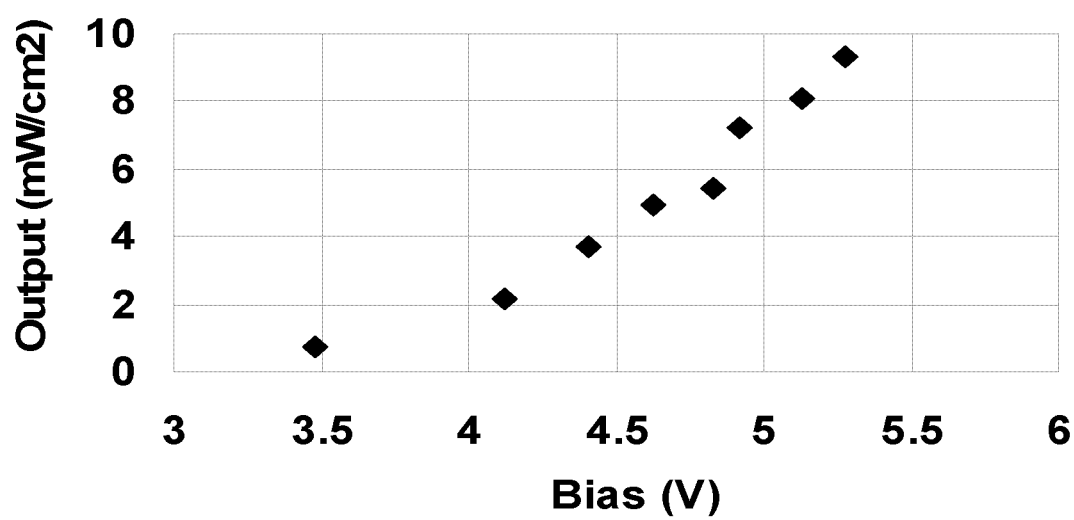
FIG. 12 is a plot of light output as a function of bias of an embodiment of a light-emitting device.

Performance of the Device D was evaluated. FIG. 9 is the electroluminescence spectrum of the device. FIG. 10 is a plot of luminance and light power output as a function of current density. The plot shows that the light power output of the device is sufficient for phototherapy at a current density range that may be used for that application. FIG. 11 is a plot of current efficiency and power efficiency as a function of luminance. FIG. 12 is a plot of light output as a function of bias. The plot shows that the light output is sufficient for phototherapy at a luminance range that may be used for that application. The turn-on voltage for the device was about 2.6 volts and the maximum luminance was about 11,500 cd/m$^2$ with 1.8 cm$^2$ area device at about 5.4V. The EQE (external quantum efficiency), luminous efficiency and power efficiency of the device at 1000 cd/m$^2$ were about 15%, 12 cd/A and 11 lm/w at 630 nm emission.

Example 3

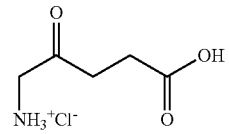

5-Aminolevulinic acid HCl

5-Aminolevulinic acid HCl (20% topical solution, available as LEVULAN® KERASTICK® from DUSA® Pharmaceuticals) is topically applied to individual lesions on a person suffering from actinic keratoses. About 14-18 hours after application, the treated lesions are illuminated with a red light-emitting OLED device constructed as set forth in Example 2.

After the treatment, the number or severity of the lesions is anticipated to be reduced. The treatment is repeated as needed.

Example 4

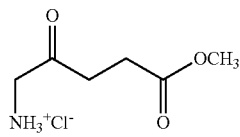

Methyl Aminolevulinate

Methyl aminolevulinate (16.8% topical cream, available as METVIXIA® Cream from GALERMA LABORATORIES, Fort Worth, Tex., USA) is topically applied to individual lesions on a person suffering from actinic keratoses. The excess cream is removed with saline, and the lesions are illuminated with the red light-emitting OLED constructed as set forth in Example 2.

Nitrile gloves are worn at all times during the handling of methyl aminolevulinate. After the treatment, it is anticipated that the number or severity of the lesions is reduced. The treatment is repeated as needed.

Example 5

Verteporphin is intravenously injected, over a period of about 10 minutes at a rate of about 3 mL/min, to a person suffering from age-related macular degeneration. The verteporphin (7.5 mL of 2 mg/mL reconstituted solution, available as Visudyne® from Novartis) is diluted with 5% dextrose to a volume of 30 mL using a sufficient quantity of the reconstituted verteporphin so that the total dose injected is about 6 mg/m$^2$ of body surface.

About 15 minutes after the start of the 10 minute infusion of verteporphin, the verteporphin is activated by illuminating the retina with a red light-emitting OLED device as set forth in Example 2.

After treatment, the patient's vision is anticipated to be stabilized. The treatment is repeated as needed.

Example 6

Verteporphin is intravenously injected, over a period of about 10 minutes at a rate of about 3 mL/min, to a person suffering from pathological myopia. The verteporphin (7.5 mL of 2 mg/mL reconstituted solution, available as Visudyne® from Novartis) is diluted with 5% dextrose to a volume of 30 mL using a sufficient quantity of the reconstituted verteporphin so that the total dose injected is about 6 mg/m$^2$ of body surface.

About 15 minutes after the start of the 10 minute infusion of verteporphin, the verteporphin is activated by illuminating the retina with a red light-emitting OLED device as set forth in Example 2.

After treatment, the patient's vision is anticipated to be stabilized. The treatment is repeated as needed.

Example 7

Verteporphin is intravenously injected, over a period of about 10 minutes at a rate of about 3 mL/min, to a person suffering from presumed ocular histoplasmosis. The verteporphin (7.5 mL of 2 mg/mL reconstituted solution, available as Visudyne® from Novartis) is diluted with 5% dextrose to a volume of 30 mL using a sufficient quantity of the reconstituted verteporphin so that the total dose injected is about 6 mg/m$^2$ of body surface.

About 15 minutes after the start of the 10 minute infusion of verteporphin, the verteporphin is activated by illuminating the retina with a red light-emitting OLED device (such as Device-A).

After treatment, the patient's vision is anticipated to be stabilized. The treatment is repeated as needed.

Example 8

Ex-Vivo Efficacy Study with Device A

Figure 13:
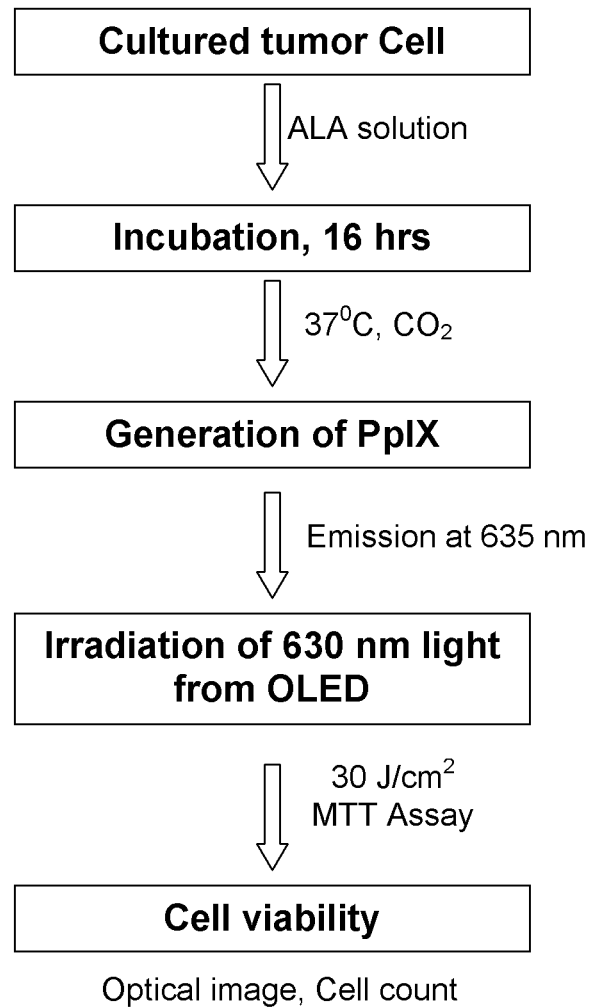
FIG. 13 is a schematic representation of ex-vivo efficacy study of an embodiment of a light-emitting device.

An efficacy study has been performed on CHO-K1 (Chinese Hamster Ovarian Cancer, ATCC, CRL-2243) cell line using the pro-drug 5-aminolevulinic acid (ALA). FIG. 13 exhibits the efficacy study scheme. Cells were cultured in a 96-well media (Hyclone F-12K medium and dulbeccdo phosphate buffer saline, DPBS) and incubated at 37° C. under $CO_2$ atmosphere for about 24 hrs. The cells were calibrated by cell counting with a standard cross area under optical microscope (Olympus IX-70) to establish a base reference number of cells of about 10,000 counts in 100 uL medium per well plate. ALA solutions (0.84 mg/mL~3.3 mg/mL in F-12K medium) with three different concentrations: 0.5 mM, 1 mM, and 2 mM, were introduced into same media as mentioned above and incubated for about 16 hrs at 37° C. under a $CO_2$ atmosphere. While not being limited by theory, it is believed that in this process, ALA undergoes a biological transformation and is converted to protoporphyrin IX (PpIX). The generation of PpIX was confirmed by fluorescence emission at 635 nm.

Figure 14A:
FIGS. 14A and 14B shows the image of Chinese Hamster Ovarian Cancer cells before and after the light irradiation from OLED.
Figure 14B:

An OLED was constructed similar to those of Example 2 (emissive layer comprising Compound X:Ir(piq)$_2$acac) (Device A). Red light (630 nm) was then generated by the OLED to provide a total dose of about 15 to 60 J/cm$^2$ with variable output power ranging from 5 mW/cm$^2$ to 20 mW/cm$^2$. While not being limited by theory, it is believed PpIX absorbs 630 nm light and is excited to its singlet state followed by inter-system crossing to triplet state. While not being limited by theory, it is believed that since the triplet state may have a longer lifetime, the triplet PpIX may interact with molecular oxygen and may generate singlet oxygen and other reactive oxygen species (ROS). These ROS may have a shorter lifetime and may have a diffusion length of only about several tens of nm. The ROS within their area may then undergo cytotoxic reaction with different cell components such as cell membrane, mitochondria, lissome, golgy bodies, nucleus etc and may destroy them and ultimately tumor cell dies. Optical microscope (Olympus IX-70) images of the cells after about 25 J/cm$^2$ red light irradiation shows (FIG. 14) that the healthy leafy type cells (FIG. 14A) transforms to droplet type upon light irradiation (FIG. 14B) indicating a significant and irreversible cell death.

Figure 15:
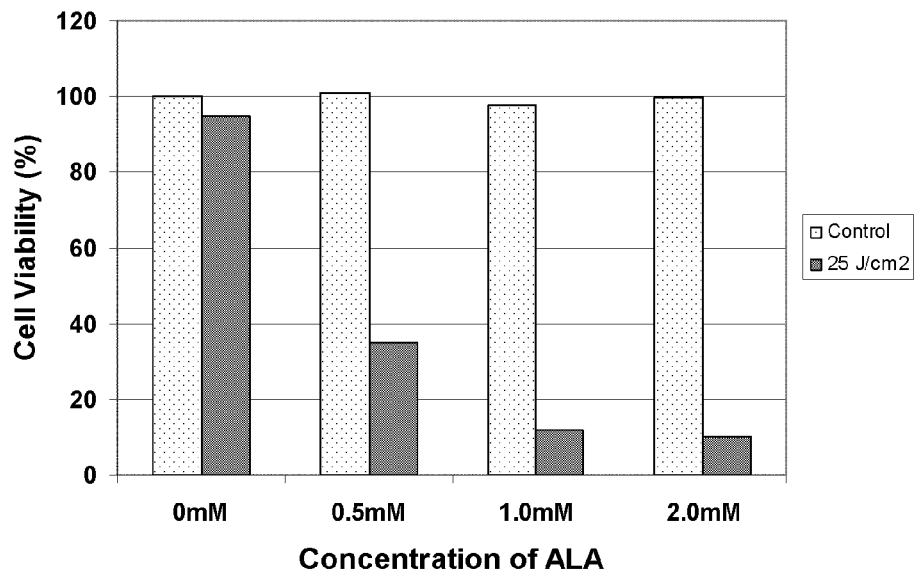
FIG. 15 shows cell viability (%) data with respect to the varying concentration of 5-ALA solution under same irradiation dose (25 J/cm2).

Following light irradiation, 10 uL of MTT solution (Invitrogen, 3,(4,5-dimethylthiazol-2-yl)-2,5-diphenyl tetrazolium bromide, 5 mg/mL in DPBS) was added to each well including the control well and shaken well to mix precisely. The wells were incubated (37° C., 5% $CO_2$) for 1.5 hrs to generate purple crystals. Then 100 uL MTT solubilization solutions were added to each well and incubated (37° C., 5% $CO_2$) for 16 hrs to dissolve the purple crystals. Finally the absorbance of the cells at 570 nm with a reference wavelength at 690 nm were recorded by a microplate reader (BioTeK MQX-200) in order to estimate cell viability (%). Cell viability results are shown in FIG. 15. At ALA concentrations of about 1 mM or higher, almost 90% of cells were destroyed as compared to the reference cells. The reference cells were irradiated with same dose of light but without ALA. Identical cells were also kept at normal environment without light irradiation and compared with reference.

Figure 16:
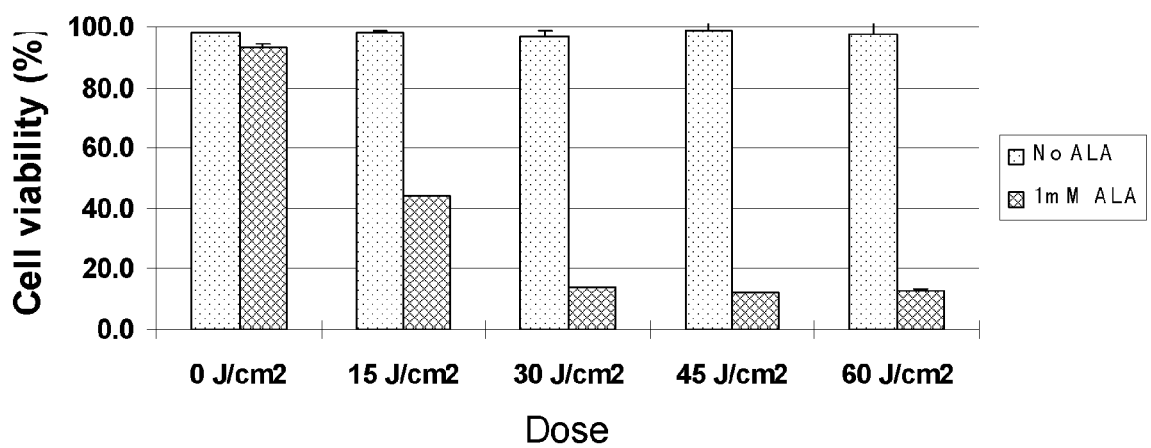
FIG. 16 shows cell viability (%) data with respect to the varying dose of irradiation with same concentration of ALA solution (1 mM).
Figure 17:
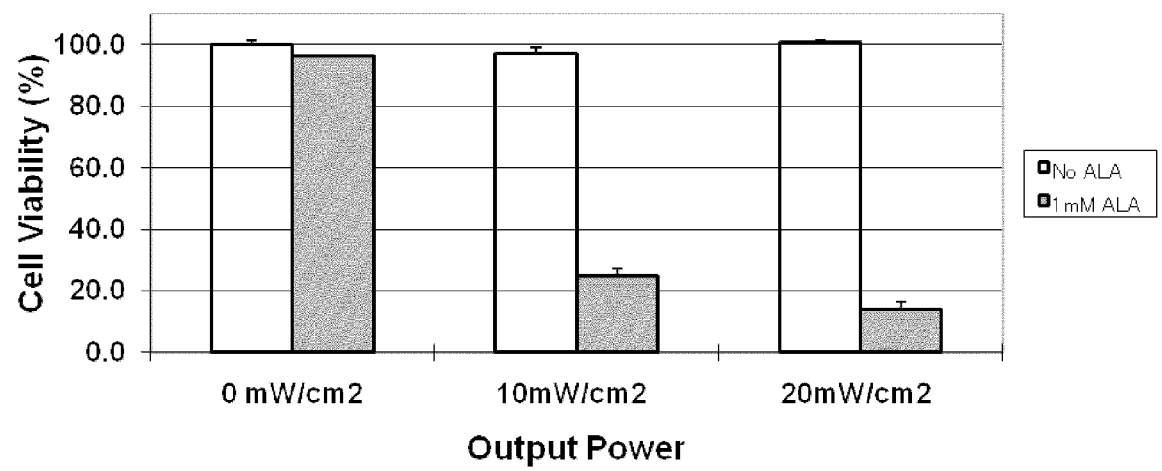
FIG. 17 shows cell viability (%) data with respect to the varying output power (mW/cm2) with same concentration of ALA solution (1 mM).

Light Dosimetry was used to optimize the irradiation dose. FIG. 16 shows the cell viability result compared with the reference. In this case the concentration of ALA was fixed at 1 mM and light output was fixed to 10 mW/cm2. The light dose was varied from 15 J/cm$^2$ to 60 J/cm$^2$ varying the time of exposure to the light. As shown, almost 90% cells were destroyed with a light dose above about 30 J/cm$^2$, indicating that the OLED has potential for use as a light source for PDT treatment. A light dose of about 30 J/cm$^2$ takes about 50 minutes to administer at a power output of 10 mW/cm$^2$. However, higher output power may allow the same dose, e.g. 30 J/cm$^2$, to be administered in less irradiation time. FIG. 17 exhibits the cell viability study with two typical outputs as 10 mW/cm$^2$ and 20 mW/cm$^2$ after an irradiation time of 50 min and 25 min, respectively. As shown, the cell necrosis was somewhat faster with 20 mW/cm$^2$ than 10 mW/cm$^2$. Higher output power is believed to accelerate the generation of ROS, which is believed to accelerate cell necrosis.

Although the subject matter of the claims have been disclosed in the context of certain embodiments and examples, it will be understood by those skilled in the art that the scope of the claims extends beyond the specifically disclosed embodiments to other alternative embodiments and/or uses of the invention and obvious modifications and equivalents thereof. Thus, it is intended that the scope of the present claims should not be limited by the particular disclosed embodiments described above.

What is claimed is:

1. A phototherapy device comprising a light-emitting device, wherein the light-emitting device comprises:
   a light-emitting layer comprising a compound selected from the group consisting of:

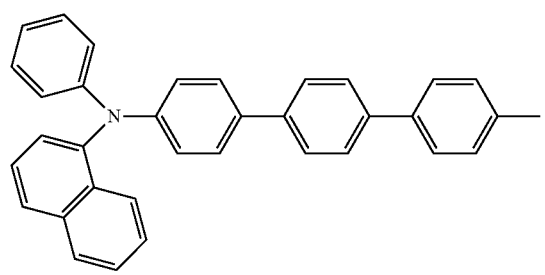

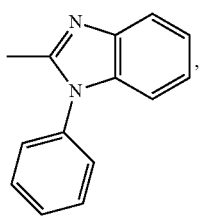

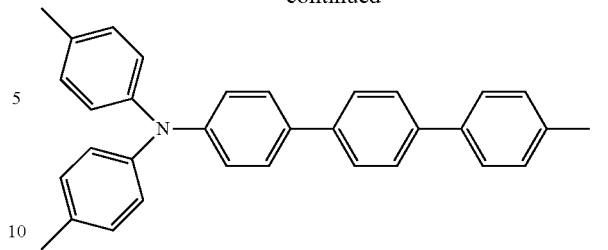

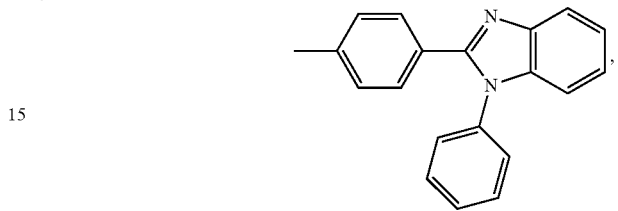

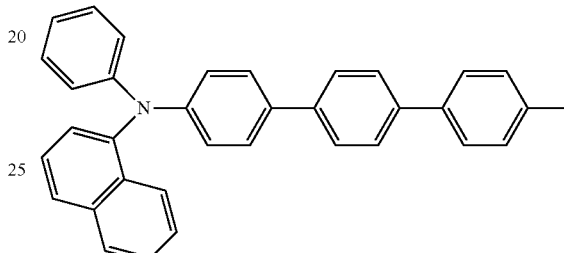

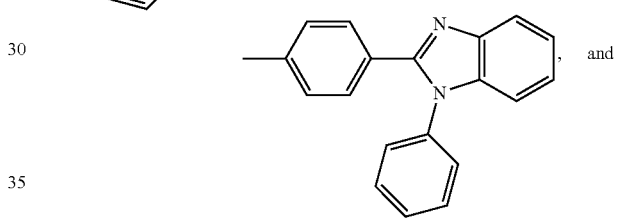, and

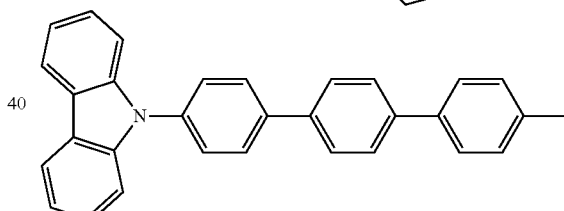

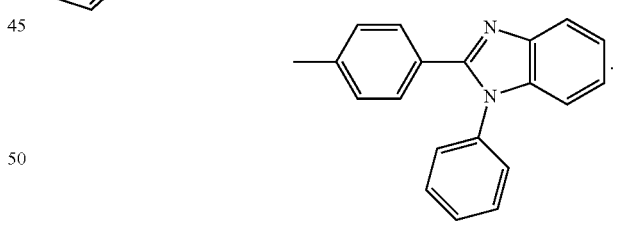

2. The phototherapy device claim 1, wherein the light-emitting device is configured to emit light of a wavelength that can activate at least a portion of a photosensitive compound which has been administered to a tissue of a mammal; and
   wherein the phototherapy device further comprises a dosage component configured to control amount of light to activate a portion of the photosensitive compound to provide a therapeutic effect.

3. The phototherapy device of claim 2, wherein the dosage component comprises a timer.

4. A phototherapy system comprising:
   a phototherapy device according claim 1; and
   a wound dressing.

5. The phototherapy system of claim 4, further comprising a dosage component configured to control a therapeutically effective amount of light.

6. The phototherapy system of claim 4, wherein the device comprises:

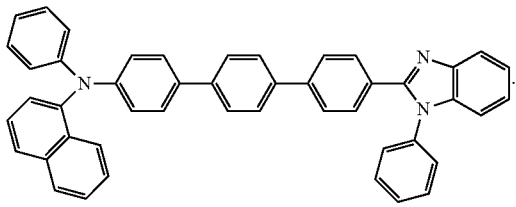 [SMILES: c1ccc(N(c2ccc(-c3ccc(-c4ccc(-c5nc6ccccc6n5-c5ccccc5)cc4)cc3)cc2)c2cccc3ccccc23)cc1]

7. The phototherapy system of claim 4, wherein the device comprises:

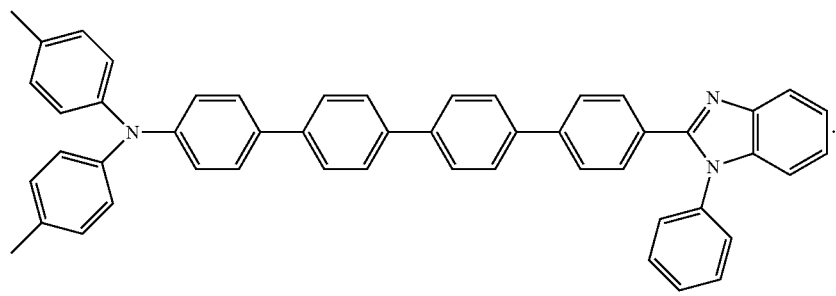 [SMILES: Cc1ccc(N(c2ccc(C)cc2)c2ccc(-c3ccc(-c4ccc(-c5ccc(-c6nc7ccccc7n6-c6ccccc6)cc5)cc4)cc3)cc2)cc1]

8. The phototherapy system of claim 4, wherein the device comprises:

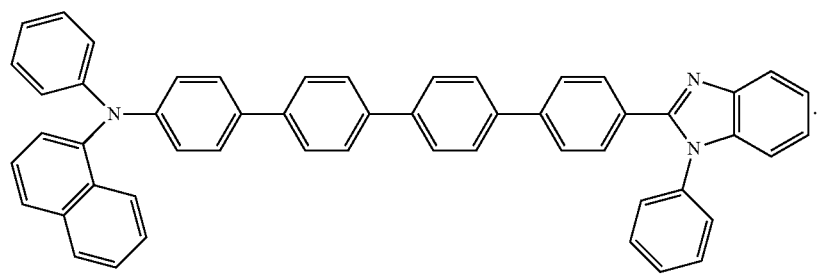 [SMILES: c1ccc(N(c2ccc(-c3ccc(-c4ccc(-c5ccc(-c6nc7ccccc7n6-c6ccccc6)cc5)cc4)cc3)cc2)c2cccc3ccccc23)cc1]

9. The phototherapy system of claim 4, wherein the device comprises:

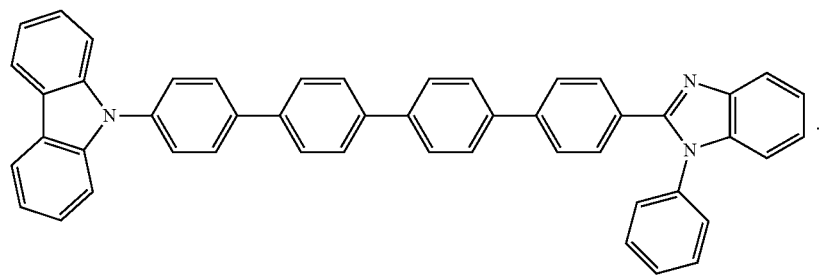 [SMILES: c1ccc(-n2c(-c3ccc(-c4ccc(-c5ccc(-c6ccc(-n7c8ccccc8c8ccccc87)cc6)cc5)cc4)cc3)nc3ccccc32)cc1]

10. A method of carrying out phototherapy comprising exposing at least a portion of a tissue of a mammal to light from a device of claim 1.

11. The method of claim 10, further comprising administering a photosensitive compound to the tissue, and wherein at least a portion of the photosensitive compound is activated by exposing the portion of the tissue to light from the device.

12. A method of treating a disease selected from the group consisting of cancer, microbial infection, skin condition, or eye condition, comprising:
   administering a photosensitive compound to a tissue of a mammal in need thereof;
   exposing at least a portion of the tissue to light from a device of claim 1: and
   activating at least a portion of the photosensitive compound by at least a portion of the light from the device, to thereby treat the disease.

13. The method of claim 12, wherein activating at least a portion of the photosensitive compound produces singlet oxygen.

14. The method of claim 12, wherein the photosensitive compound is 5-amninolevulinic acid, verteporfin, zinc phthalocyanine, or pharmaceutically acceptable salts thereof.

15. The method of claim 14, wherein the photosensitive compound is 5-aminolevulinic acid.

16. The method of claim 15, wherein the 5-aminolevulinic acid is present in the tissue at a concentration of about 0.5mM to about 2mM.

17. The method of claim 16, wherein the device has a peak emission of about 630 nm.

18. The method of claim 17, wherein the tissue receives a light dose that is at least about 30 Joules/cm$^3$.

19. The method of claim 18, wherein the tissue receives a light dose that is in the range of about 30 Joules/cm$^3$ to about 60 Joules/cm$^3$.

20. A phototherapy system comprising:
A phototherapy device according to claim 1; and
a photosensitive compound;
wherein the photosensitive compound is suitable for administration to a tissue of a mammal in need of phototherapy; and
wherein the phototherapy device is configured to emit light of a wavelength which can activate at least a portion of the photosensitive compound when the photosensitive compound is in the tissue.

21. The phototherapy system of claim 20, wherein the photosensitive compound is 5-aminolevulinic acid, verteporfin, zinc phthalocyanine, or pharmaceutically acceptable salts thereof.

* * * * *